United States Patent [19]

Magolda et al.

[11] Patent Number: 5,874,441
[45] Date of Patent: Feb. 23, 1999

[54] CARBOCYCLIC AND HETERTOCYCLIC FUSED-RING QUINOLINECARBOXYLIC ACIDS USEFUL AS IMMUNOSUPPRESSIVE AGENTS

[75] Inventors: Ronald Louis Magolda, Wallingford; William John Pitts, Conshohocken; Irina Cipora Jacobson, Boothwyn, all of Pa.; Carl Henry Behrens, Newark, Del.; Michael James Orwat; Douglas Guy Batt, both of Wilmington, Del.

[73] Assignee: DuPont Pharmaceuticals Company, Wilmington, Del.

[21] Appl. No.: 820,222

[22] Filed: Mar. 18, 1997

Related U.S. Application Data

[62] Division of Ser. No. 411,251, Mar. 27, 1995, Pat. No. 5,639,759, which is a division of Ser. No. 114,712, Aug. 31, 1993, Pat. No. 5,428,040.

[51] Int. Cl.$^6$ .......................... A01N 43/42; C07D 471/00
[52] U.S. Cl. ............................ 514/285; 514/287; 546/64; 546/70
[58] Field of Search ................ 546/64, 70; 514/285, 514/287

[56] References Cited

U.S. PATENT DOCUMENTS

| | | | |
|---|---|---|---|
| 4,680,299 | 7/1987 | Hesson | 514/311 |
| 4,847,381 | 7/1989 | Sutherland et al. | 546/156 |
| 4,918,077 | 4/1990 | Behrens | 514/284 |
| 4,968,701 | 11/1990 | Ackerman et al. | 514/312 |
| 4,968,702 | 11/1990 | Poletto et al. | 514/313 |
| 5,135,934 | 8/1992 | Behrens | 514/297 |
| 5,304,554 | 4/1994 | Strekowski et al. | 514/228.2 |

FOREIGN PATENT DOCUMENTS

WO93 22286  11/1993  WIPO.

OTHER PUBLICATIONS

Jadwign Schoen and Krystynn Bogdanowicz–Szwed., Chemical Abstracts 61:1827g.
E. Noelting and A. Herzbaum., Chem. Ber. vol. 44, 2585, 1991.
N. P. Buu–Hoi, V. Bellavita, A. Ricci, J. P. Hoeffinger and D. Balucani., J. Chem. Soc.(C), 47, 1966.
Kamane Takagi et Takeo Ueda., Chem. Pharm. Bull, vol.19, 1218, 1971.
Kamane Takagi et Takeo Ueda., Chem. Pharm. Bull, vol.20, 2051, 1972.
Ng. Ph. Buu–Hoi., J. C. S., 2418, 1958.
par Paul Cagniant, Alfred Reisse(**) et Denise Cagniant., Bulletin Se La Societe Chimique De France, 991, (1969). [Bull. Soc. Chem. France, 991, (1969)].
par Paul Cagniant, Guy Merle(**) et Denise Cagniant., Bulletin Se La Societe Chimique De France, 322, (1970). [Bull. Soc. Chem. France, 322, (1970)].
Von Rolf Huisgen, Ivar Ugi., Liebigs Ann. Chem. Bd., 610, 57, (1957).
Kinoshita Yukihiko, Ajisawa Yukiyoshi, Ikeguchi Seiichi, Ujiie Shinsei and Tsutsimi Naoyuki., 1–Pharmacology, vol. 111:187618h, (1989).
Seiji Yamaguchi, Kunihiro Tsuzuki, Yoshie Sannomiya, Yutaka Oh–hira and Yoshiyuki Kawase., J. Heterocyclic Chem., 26, 285, (1989).
Degutis J, Ezerskaite A., Chemical Abstracts vol.107:39658y, (1987).
Ezerskaite A, Degutis J, Undzenas A, Kalcheva V., Chemical Abstracts vol.112: 66492z, (1990).
Ezerkaite A, Kalcheva V, Peshakova L., 28–Heterocycles vol.113:58979u, (1990).
Fravolini Arnaldo, Rodriguez Salazar Carlos., Chemical Abstracts vol.70:47334x, (1969).
Fravolini Arnaldo, Rodriguez Salazar Carlos., Ann. Chim.(Rome) vol. 58, 1155–62, (1968).
Wang Jinjun, Yin Bingzhu, Jiang Guiji., Chemical Abstracts vol.115:49457m, (1991).
Wang Jinjun, Jiang Guiji, Fang Wenlong, Jin Jingji., Chemical Abstracts vol.115:183138m, (1991).
Odette Roussel, N.P. Buu–Hoi and P. Jacquignon., J. Chem. Soc., 5458, (1965).
Antonio Da Settimo, Giampaolo Primofiore, Orsete Livi, Pier Luigi Ferrarini and Silvano Spinelli., J. Heterocyclic Chemistry, vol.16, 169–174, (1979).
John T. Brauholtz and Fredrick G. Mann., J. Chem. Soc., 3377, (1958).
George R. Procter and Brian M.L.Smith., J.C.S. Perkin I, 862–870, (1978).
S. J. Holt and V. Petrow., J.C.S., 607–611, (1947).
John T. Brauholtz and Fredrick G. Mann., J. C. S., 381–392, (1955).
Fredrick G. Mann., J.C.S., 2816–2824, (1949).
Julius V. Braun and Karl Weissbach., Chem. Ber. vol.62, 2416–2425, (1929).
A. K. Kiang and Fredrick G. Mann., J.C.S. 1909–1914, (1951).
N.P. Buu–Hoi and G. Saint–Ruf., 38–Heterocyclic Compounds 11998, (1964).
D. Huckle, I. M. Lockhart and N.E. Webb., J. Chem. Soc.(C), 2252–2260, (1971).
Hoi Jirul. Wang Jinjun, Jiang Guiji, Li Jingahu., 29–Heterocycles vol.116:128709u, (1992).

*Primary Examiner*—Mukund J. Shah
*Assistant Examiner*—Tamthom T. Ngo

[57] ABSTRACT

This invention relates to carbocyclic and heterocyclic fused-ring quinolinecarboxylic acid compounds, to pharmaceutical compositions comprising such compounds, and to methods of using such compounds for the treatment and/or prevention of organ transplantation rejection, graft versus host disease, autoimmune diseases, chronic inflammatory diseases, including but not limited to psoriasis and rheumatoid arthritis, and cancer in a mammal.

19 Claims, No Drawings

CARBOCYCLIC AND HETEROCYCLIC FUSED-RING QUINOLINECARBOXYLIC ACIDS USEFUL AS IMMUNOSUPPRESSIVE AGENTS

This is a division of application Ser. No. 08/411,251, filed Mar. 27, 1995, now U.S. Pat. No. 5,639,759 which is a division of application Ser. No. 8/114,712, filed on Aug. 31, 1993 now U.S. Pat. No. 5,428,040.

FIELD OF THE INVENTION

This invention relates to carbocyclic and heterocyclic fused-ring quinolinecarboxylic acid compounds, to pharmaceutical compositions comprising such compounds, and to methods of using such compounds for the treatment and/or prevention of organ transplantation rejection, graft versus host disease, autoimmune diseases, and chronic inflammatory diseases, including but not limited to psoriasis and rheumatoid arthritis, in a mammal.

BACKGROUND OF THE INVENTION

2-Phenyl-4-quinolinecarboxylic acids are disclosed as tumor-inhibiting agents by U.S. Pat. No. 4,680,299, issued to Hesson on Jul. 14, 1987. Utility of these compounds for the treatment of skin and epithelial diseases is disclosed by U.S. Pat. No. 4,861,783, issued to Ackerman et al. on Aug. 29, 1989. Utility of these compounds as immunomodulatory or immunosuppressive agents is disclosed by U.S. Pat. No. 4,968,701, issued to Ackerman et al. on Nov. 6, 1990. U.S. Pat. No. 5,204,329, issued to Ackerman et al. on Apr. 20, 1993, describes the use of these compounds in combination with a second immunosuppressive agent for the treatment of transplantation rejection and other disease conditions.

Additional examples of 2-phenyl-4-quinolinecarboxylic acids are disclosed as useful in the treatment of arthritis and for inducing immunosuppression in U.S. Pat. No. 4,847,381, issued to Sutherland et al. on Jul. 11, 1989; and in U.S. Pat. No. 4,968,702, issued to Poletto et al. on Nov. 6, 1990.

Benz[c]acridine-7-carboxylic acids and 5,6-dihydrobenz [c]acridine-7-carboxylic acids are known in the chemical literature. They are generally synthesized by the Pfitzinger reaction of an appropriate isatin with an appropriate 3,4-dihydro-1(2H)-naphthalenone. U.S. Pat. No. 4,918,077, issued to Behrens on Apr. 17, 1990, discusses a number of references dealing with these compounds, and also discloses tumor-inhibiting 3-phenyl-5,6-dihydrobenz[c]acridine-7-carboxylic acids of the formula:

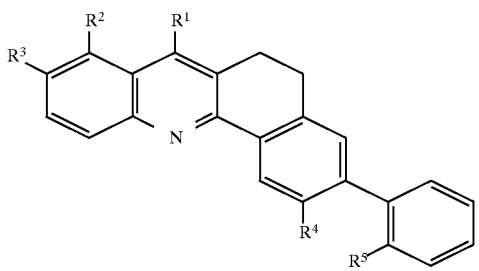

where $R^1$ is, inter alia, COOH, COONa or COOK; $R^2$ and $R^3$ are independently H, F, Cl, Br, I, methyl, ethyl, $CF_3$, alkylthio, alkylsulfinyl, or alkylsulfonyl; and $R^4$ and $R^5$ independently are H or taken together are S. U.S. Pat. No. 5,135,934, issued to Behrens et al. on Aug. 4, 1992, discloses the utility of these compounds as immunosuppressive and anti-inflammatory agents.

The synthesis of ring-fused quinolinecarboxylic acids of the formula:

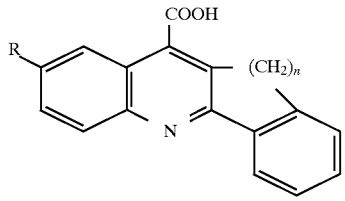

where n is 1–4, and R is H or methyl, h as also been reported by Huisgen et al. [*Ann. Chem.* (1957) 610:57] and Schoen et al. [*Rocz. Chem.* (1964) 38:425; *Chem. Abstr.* 61, 1827g]. Noelting et al. [*Chem. Ber.* (1911) 44:2585] reported the synthesis of these compounds also, as well as of the compound where R is H and where $(CH_2)_n$ has been replaced by S. The same compound, but where R is methyl and $(CH_2)_n$ is replaced by S, was synthesized by Buu-Hoi [*J. Chem. Soc.* C (1966) 47] as an intermediate to potential carcinogens.

The synthesis of 4,5-dihydrofuro [2,3-c]acridine-6-carboxylic acids of the formula:

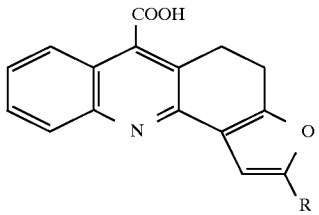

where R is methyl, phenyl, or 4-bromophenyl, has been reported by Takagi et al. [*Chem. Pharm. Bull.* (1971) 19:1218, and *Chem. Pharm. Bull.* (1972) 20:2051].

Buu-Hoi et al. [*J. Chem. Soc.* (1958) 2418] reported the synthesis of the compound shown below as an intermediate for potential carcinogens.

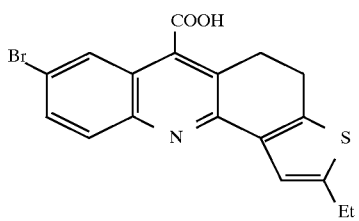

Cagniant et al. [*Bull. Soc. Chim. Fr.* (1969) 991, and *Bull. Soc. Chim. Fr.* (1970) 322] reported the synthesis of other thienoacridine analogs of the formula:

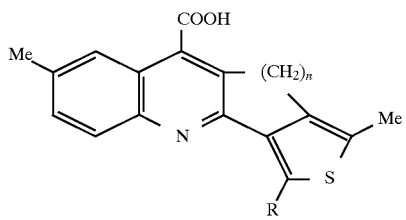

where R is H or methyl and n is 1 or 2.

The compound shown below was reported by Braunholtz et al. [*J. Chem. Soc.* (1962) 4346] as a synthetic intermediate.

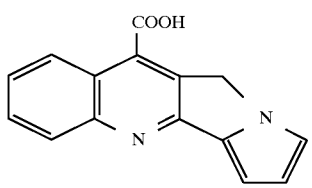

Benzofuro [3,2-b quinolines of the formula:

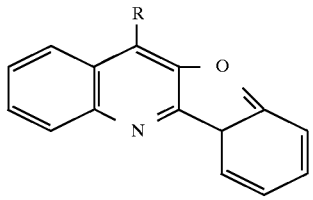

where R is lower alkyl or carboxy are disclosed in Jpn. Kokai Tokkyo Koho 63,295,579, issued to Kinoshita et al. on Dec. 1, 1988 [*Chem. Abstr.* 111, 187618], with utility in the treatment of osteoporosis. Analogous carboxylic acids substituted with a single halogen atom, as well as the corresponding N-oxides, were synthesized by Yamaguchi et al. (*J. Heterocyclic Chem.* (1989) 26:285] as intermediates to potential carcinogens, mutagens and antitumor substances. An additional compound of the same formula, where R is COOH, where a methoxy substituent is present on the benzofuran ring, and where the O has been replaced by S, has also been synthesized by Buu-Hoi et al. [*Israel J. Chem.* (1963) 1:369; *Chem. Abstr.* 60, 11998f].

Degutis et al. [*Khim. Geterotsikl. Soedin.* (1986) 1375; *Chem. Abstr.* 107, 39658] and Ezerskaite et al. [*Izv. Khim.* (1989) 22:113; *Chem. Abstr.* 112, 66492, and *Izv. Khim.* (1989) 22:232; *Chem. Abstr.* 113, 58979] synthesized indoloquinoline carboxylic acids of the formula:

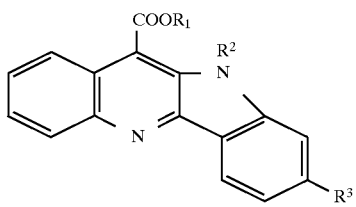

where $R^1$ and $R^2$ are H or alkyl and $R^3$ is H or bromo, and disclosed utility as sensitizers for electrophotography.

Holt et al. [*J. Chem. Soc.* (1947) 607] also discuss the synthesis of this type of compound.

Fravolini et al. [*Ann. Chim.* (1968) 58:1155; *Chem. Abstr* 70, 47334] synthesized the fluorinated benzothiopyrano-quinoline carboxylic acids shown below.

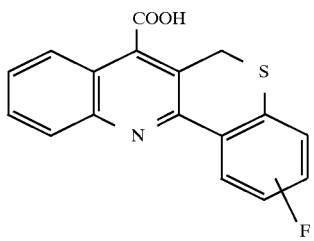

Hou et al. [*Youji Huaxue* (1991) 11:615; *Chem. Abstr.* 116, 128709] reported the synthesis of the compounds shown below, where R is H or halogen.

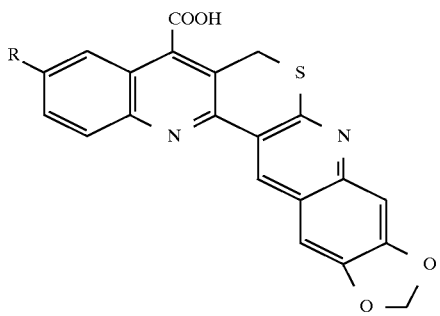

Wang et al. [*Gaodeng Xuexiao Huaxue Xuebao* (1991) 12:59; *Chem. Abstr.* 115, 49457, and *Zhongguo Yiyao Gongye Zashi* (1991) 22:103; *Chem. Abstr.* 115:1831381 disclosed the synthesis and anti-inflammatory activity of 7-carboxyisochromano[4,3-b]quinolines of the formula:

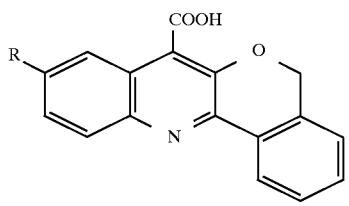

where R is H, halogen or methyl. A compound of this formula, but lacking the R group and with O replaced by S, was synthesized by Braun et al. [*Chem. Ber.* (1929) 62:2416] and by Kiang et al. [*J. Chem. Soc.* (1951) 1909]. No utility was reported for this latter compound.

Roussel et al. [*J. Chem. Soc.* (1965) 5458] reported the synthesis of dibenzonaphthyridine derivatives of the formula:

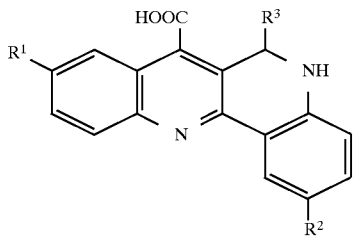

where $R^1$ is H, methyl or chloro; $R^2$ is H, methoxy or chloro, and $R^3$ is H or methyl, as potential carcinogens.

The quinolinonaphthyridine derivatives show below (R=H, acetyl) were reported by Settimo et al. (*J. Heterocyclic Chem.* (1979) 16:169].

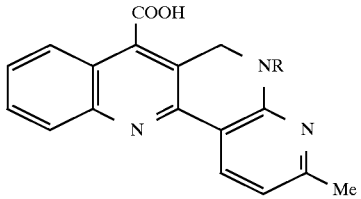

Synthesis of similar compounds, lacking the methyl substituent shown above but where R is methyl or phenyl, have been reported by Braunholtz et al. [*J. Chem. Soc.* (1955) 381] and Mann [*J. Chem. Soc.* (1949) 2816], respectively.

The benzoquinolinoazepine derivatives of the formula:

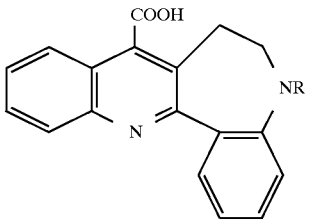

where R is methyl or tosyl have been synthesized by Braunholtz et al. [*J. Chem. Soc.* (1958) 33773] and by Proctor et al. [*J. Chem. Soc. Perkin Trans. I* (1978) 862], respectively. Another compound of this formula, but with NR replaced by S, was synthesized by Huckle et al. [*J. Chem. Soc. C* (1971) 2252].

There are no literature references disclosing the ring-fused quinolinecarboxylic acids or derivatives thereof of the present invention, or their use in treating and/or preventing immunologic disorders.

Presently, cyclosporin A, an immunosuppressive agent, used in combination with other adjunctive therapies, such as azathioprine and corticosteroids, is the treatment of choice for the prevention of organ transplantation rejection. Other immunosuppressive agents such as azathioprine, corticosteroids (such as prednisone), OKT3, FK506, mycophenolic acid or the 2-(N-morpholino)ethyl ester thereof, 15-deoxyspergualin, rapamycin, mizoribine, misoprostol and anti-interleukin-2 receptor antibodies, have been used or have been suggested to be useful in the treatment and/or prevention of organ transplantation rejection.

Use of any of these known immunosuppressive compounds, either alone or in combination, is associated with a high incidence of side effects such as nephrotoxicity and/or hepatoxicity. Thus, there presently exists a need for improved therapies for the treatment of cancer and for the treatment and/or prevention of organ transplantation rejection, graft versus host disease, autoimmune diseases, and chronic inflammatory diseases, including but not limited to psoriasis and rheumatoid arthritis.

It has now been found that the carbocyclic and heterocyclic fused-ring quinolinecarboxylic acid compounds described herein are useful for the treatment and/or prevention of organ transplantation rejection, graft versus host disease, autoimmune diseases, and chronic inflammatory diseases, including but not limited to psoriasis and rheumatoid arthritis, in a mammal.

The carbocyclic and heterocyclic fused-ring quinolinecarboxylic acid compounds of this invention can be used alone or in combination with one or more additional known immunosuppressive agents, such as cyclosporin A (CSA or CsA) and analogs thereof, FK506 (or FK-506) and analogs thereof, corticosteroids, azathioprine (AZA), mycophenolic acid or the 2-(N-morpholino)ethyl ester thereof, mycophenolate mofetil, rapamycin, 15-deoxyspergualin, mizoribine, leflunomide, OKT3, anti-interleukin-2 receptor antibodies, misoprostol, methotrexate, cyclophosphamide, and anti-lymphocyte/thymocyte serums, thereby to reduce the dosage required and associated adverse effects of these immunosuppressive agents.

SUMMARY OF THE INVENTION

This invention relates to carbocyclic and heterocyclic fused-ring quinolinecarboxylic acid compounds of Formulas 1–4 described below, to pharmaceutical compositions comprising such compounds, and to methods of using such compounds for the treatment and/or prevention of organ transplantation rejection, graft versus host disease, autoimmune diseases, and chronic inflammatory diseases, including but not limited to psoriasis and rheumatoid arthritis, in a mammal. The compounds of Formulas 1–4 of the present invention are also useful for the treatment of tumors in a mammal.

The compounds of Formulas 1–4 described herein have been discovered to be immunosuppressive or immunomodulatory agents which are useful for the treatment and/or prevention in a mammal of organ transplantation rejection, graft versus host disease, and autoimmune diseases, including but not limited to systemic lupus erythematosus, rheumatoid arthritis, psoriasis, multiple sclerosis, and myasthenia gravis. The compounds of Formulas 1–4 of the present invention are also useful for the treatment and/or prevention in a mammal of chronic inflammatory diseases, including but not limited to Crohn's disease, inflammatory bowel disease, rheumatoid arthritis, psoriasis, and primary biliary cirrhosis. The compounds of Formulas 1–4 of the present invention are also useful for the treatment of tumors in a mammal, including leukemias and solid tumors, including tumors of the breast, colon, and lung.

The present invention also provides pharmaceutical compositions comprising a compound of Formulas 1–4 and a pharmaceutically acceptable carrier.

Also provided in the present invention are methods of treatment and/or prevention of organ transplantation rejection, graft versus host disease, autoimmune diseases, or chronic inflammatory diseases comprising administering to a mammal in need of such treatment and/or prevention, a therapeutically effective amount of a compound of Formulas 1–4 of the present invention.

The present invention also provides methods of treatment and/or prevention of organ transplantation rejection, graft versus host disease, psoriasis, autoimmunediseases, and chronic inflammatory diseases in a mammal comprising administering to the mammal in a therapeutically effective amount for the treatment of a desired aforesaid disease a combination of: (i) a compound of Formulas 1–4 as described below and (ii) at least one additional immunosuppressive agent. Such additional immunosuppressive agent may be selected from the group including but not limited to cyclosporin A (CSA or CsA) and analogs thereof, FK506 and analogs thereof, corticosteroids, azathioprine (AZA), mycophenolic acid or the 2-(N-morpholino)ethyl ester thereof, mycophenolate mofetil, rapamycin, 15-deoxyspergualin, mizoribine, leflunomide, OKT3, anti-interleukin-2 receptor antibodies, misoprostol, methotrexate, cyclophosphamide, and anti-lymphocyte/thymocyte serums.

The compounds of Formulas 1–4 of the present invention may also be administered in combination with a non-steroidal anti-inflammatory agent, selected from the group including but not limited to, aspirin, ibuprofen, naproxen, indomethacin, diclofenac, sulindac, piroxicam, etodolac, ketoprofen, meclofenamate, suprofen, and tolmetin, for the treatment and/or prevention of organ transplantation rejection, graft versus host disease, psoriasis, autoimmune diseases, and chronic inflammatory diseases in a mammal.

Compounds of Formulas 1–4 of the present invention may also be administered in combination with other tumor inhibiting agents, including but not limited to, 5-fluorouracil, for the treatment of tumors in a mammal.

DETAILED DESCRIPTION OF THE INVENTION

This invention relates to carbocyclic and heterocyclic fused-ring quinolinecarboxylic acid compounds of Formulas 1–4 described below, to pharmaceutical compositions comprising such compounds, and to methods of using such compounds for the treatment and/or prevention of immunologic disorders, including organ transplantation rejection, graft versus host disease, autoimmune diseases, and chronic inflammatory diseases, including but not limited to psoriasis and rheumatoid arthritis, in a mammal. The compounds of Formulas 1–4 of the present invention are also useful for the treatment of tumors in a mammal.

The compounds of Formulas 1–4 described herein have been discovered to be immunosuppressive or immunomodulatory agents which are useful for the treatment and/or prevention in a mammal of organ transplantation rejection, graft versus host disease, and autoimmune diseases, including but not limited to systemic lupus erythematosus, rheumatoid arthritis, psoriasis, multiple sclerosis, and myasthenia gravis. The compounds of Formulas 1–4 of the present invention are also useful for the treatment and/or prevention in a mammal of chronic inflammatory diseases, including but not limited to Crohn's disease, inflammatory bowel disease, rheumatoid arthritis, osteoarthritis, psoriasis, and primary biliary cirrhosis. The compounds of Formulas 1–4 of the present invention are also useful for the treatment of tumors in a mammal, including leukemias and solid tumors, including tumors of the breast, colon, and lung.

The carbocyclic and heterocyclic fused-ring quinolinecarboxylic acid compounds of the present invention are selected from compounds of Formulas 1, 2, 3, or 4 (1–4):

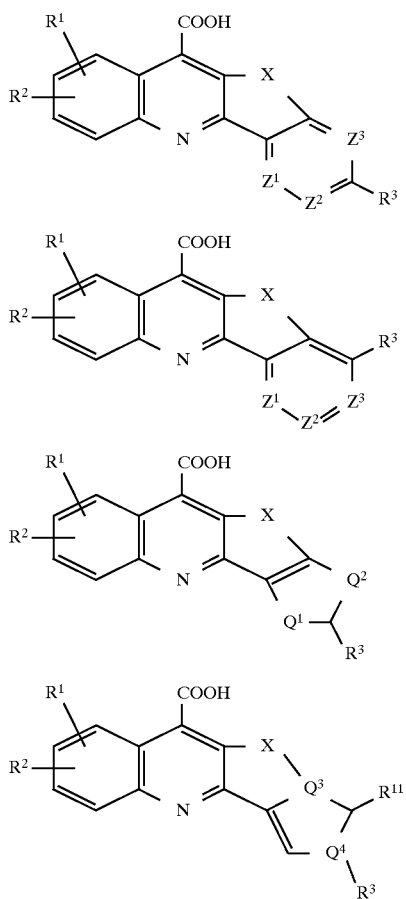

or pharmaceutically acceptable salts thereof, wherein:

$R^1$ and $R^2$ are independently selected from H, F, Cl, Br, $CF_3$, or alkyl of 1–4 carbons;

$R^3$ is selected from: phenyl, phenoxy, phenylthio, phenylsulfinyl, phenyl-N($R^4$)—, furyl, thienyl, pyridyl, thiazolyl, or oxazolyl; wherein said phenyl, phenoxy, phenylthio, phenylsulfinyl, phenyl-N($R^4$)—, furyl, thienyl, pyridyl, thiazolyl, or oxazolyl is substituted with 0–2 groups independently selected from: F, Cl, Br, $CF_3$, alkyl of 1–4 carbons, alkoxy of 1–4 carbons, alkylthio of 1–4 carbons or alkylsulfinyl of 1–4 carbons;

$R^4$ is selected from H, alkyl of 1–4 carbons or acyl of 1–4 carbons;

X is selected from —Y—, —$CH_2$Y—, —Y$CH_2$—, —$CH_2CH_2$Y—, —Y$CH_2CH_2$—, —$CH_2$Y$CH_2$—, —$CR^5$=C($R^6$)—, —$CR^6$=N—, or —N=C($R^6$)— (the first atom of X as listed being attached to the quinoline ring); wherein each methylene group in X may be optionally substituted with one or two groups independently selected from alkyl of 1–4 carbons;

Y is —$CH_2$— (said —$CH_2$— group being optionally substituted with one or two alkyl groups of 1–4 carbons), —O—, —S—, or —N($R^7$)—;

$R^5$ and $R^6$ are independently H or alkyl of 1–4 carbons;

$R^7$ is selected from H, alkyl of 1–4 carbons or acyl of 1–4 carbons;

wherein, in compounds of Formula 1 and Formula 2:

$Z^1$, $Z^2$ and $Z^3$ are independently $CR^8$ or N, with the proviso that at least one of $Z^1$, $Z^2$ and $Z^3$ is not nitrogen;

$R^8$ is independently selected from H, F, Cl, Br, $CF_3$, or alkyl of 1–4 carbons;

wherein, in compounds of Formula 3:

one of $Q^1$ and $Q^2$ is S or $NR^9$ and the other is $CR^{10}$ or N, with the stipulation that the ring which contains $Q^1$ and $Q^2$ contains an additional double bond placed so as to generate an aromatic ring;

$R^9$ is selected from H or alkyl of 1–4 carbons;

$R^{10}$ is selected from H, F, Cl, Br, $CF_3$, or alkyl of 1–4 carbons;

wherein, in compounds of Formula 4:

one of $Q^3$ and $Q^4$ is N and the other is C, with the stipulation that the ring of Formula 4 which contains $Q^3$ and $Q^4$ contains an additional double bond placed so as to generate an aromatic pyrrole ring; and $R^{11}$ is H, F, Cl, Br, $CF_3$, or alkyl of 1–4 carbons;

subject to the following provisos:

1) X is not $NR^7$;

2) in compounds of Formula 1, when X is $CH_2CH_2$ and each of $Z^1$, $Z^2$ and $Z^3$ is CH, then $R^3$ is not unsubstituted phenyl;

3) in compounds of Formula 3, or of Formula 4 where $Q^4$ is N, X must form a bridge of at least two atoms, and the atom of X attached to the ring containing $Q^1$ and $Q^2$ or $Q^3$ and $Q^4$ must be carbon;

4) in compounds of Formula 4 where $Q^3$ is N, X must consist of either —$CH_2CH_2$— or —$CH_2CH_2CH_2$—, with each methylene group of X optionally substituted as described above; and 5) in compounds of Formula 4 where $Q^4$ is N, then $R^3$ must not be phenoxy, phenylthio, phenylsulfinyl, or phenyl-N ($R^4$)—.

Preferred carbocyclic and heterocyclic fused-ring quinolinecarboxylic acid compounds of the present invention are those compounds described above of Formulas 1–4 wherein $R^1$ and $R^2$ are substituted at the 5- and/or 6-position on the quinoline ring.

Preferred carbocyclic and heterocyclic fused-ring quinolinecarboxylic acid compounds of the present invention are those compounds described above of Formulas 1–4 wherein:

$R^1$ is 6-F or 6-$CF_3$; and/or $R^2$ is H; and/or $R^3$ is phenyl, thienyl or furyl; said phenyl, thienyl or furyl being substituted with 0–2 groups independently selected from: F, Cl, Br, $CF_3$, alkyl of 1–4 carbons, alkoxy of 1–4 carbons, alkylthio of 1–4 carbons or alkylsulfinyl of 1–4 carbons; and/or X is —$CH_2CH_2$—, —$CH_2S$—, —$SCH_2$—, —$CH_2O$—, or —$OCH_2$—; and/or wherein, in compounds of Formula 1 or Formula 2, $Z^1$ is CH; and/or wherein, in compounds of Formula 3, $Q^1$ is S and $Q^2$ is CH; and/or wherein, in compounds of Formula 4, $Q^3$ is C and $Q^4$ is N.

More preferred carbocyclic and heterocyclic fused-ring quinolinecarboxylic acid compounds of Formulas 1–4 of the present invention are those preferred compounds described above wherein:

$R^3$ is phenyl, 2-fluorophenyl, 3-methoxyphenyl, 3-methylphenyl, 3-trifluoromethylphenyl, or thienyl.

Specifically preferred compounds of Formulas 1–4 of the present invention are compounds selected from the following, or a pharmaceutically acceptable salt form thereof:

(a) the compound of Formula 1 where $R^1$ is 6-F; $R^2$ is H; $R^3$ is phenyl; $Z^1$, $Z^2$ and $Z^3$ are all CH; and X is $CH_2S$; or a sodium salt;

(b) the compound of Formula 1 where $R^1$ is $CF_3$; $R^2$ is H; $R^3$ is phenyl; $Z^1$, $Z^2$ and $Z^3$ are all CH; and X is $CH_2S$, or a sodium salt;

(c) the compound of Formula 1 where $R^1$ is 6-F; $R^2$ is H; $R^3$ is 2-fluorophenyl; $Z^1$, $Z^2$ and $Z^3$ are all CH; and X is $CH_2S$, or a sodium salt;

(d) the compound of Formula 1 where $R^1$ is 6-F; $R^2$ is H; $R^3$ is 3-methoxyphenyl; $Z^1$, $Z^2$ and $Z^3$ are all CH; and X is $CH_2S$, or a sodium salt;

(e) the compound of Formula 1 where $R^1$ is 6-F; $R^2$ is H; $R^3$ is phenyl; $Z^1$, $Z^2$ and $Z^3$ are all CH; and X is $CH_2O$, or a sodium salt;

(f) the compound of Formula 1 where $R^1$ is 6-F; $R^2$ is H; $R^3$ is 3-methylphenyl; $Z^1$, $Z^2$ and $Z^3$ are all CH; and X is $SCH_2$, or a sodium salt;

(g) the compound of Formula 1 where $R^1$ is 6-F; $R^2$ is H; $R^3$ is phenyl; $Z^1$ and $Z^2$ are CH; $Z^3$ is N; and X is $CH_2CH_2$, or a sodium salt;

(h) the compound of Formula 1 where $R^1$ is 6-F; $R^2$ is H; $R^3$ is phenyl; $Z^1$, $Z^2$ and $Z^3$ are all CH; and X is $OCH_2$, or a sodium salt;

(i) the compound of Formula 1 where $R^1$ is 6-F; $R^2$ is H; $R^3$ is phenyl; $Z^1$ and $Z^2$ are CH; $Z^3$ is N; and X is $SCH_2$, or a sodium salt;

(j) the compound of Formula 1 where $R^1$ is 6-F; $R^2$ is H; $R^3$ is 2-fluorophenyl; $Z^1$, $Z^2$ and $Z^3$ are CH; and X is $CH_2CH_2$, or a sodium salt;

(k) the compound of Formula 1 where $R^1$ is 6-F; $R^2$ is H; $R^3$ is 3-trifluoromethylphenyl; $Z^1$, $Z^2$ and $Z^3$ are CH; and X is $CH_2CH_2$, or a sodium salt;

(l) the compound of Formula 1 where $R^1$ is 6-F; $R^2$ is H; $R^3$ is 3-methoxyphenyl; $Z^1$, $Z^2$ and $Z^3$ are CH; and X is $CH_2CH_2$, or a sodium salt.

The present invention also provides pharmaceutical compositions comprising a compound of Formulas 1–4 and a pharmaceutically acceptable carrier.

Also provided in the present invention are methods of treatment and/or prevention of organ transplantation rejection, graft versus host disease, autoimmune diseases, or chronic inflammatory diseases comprising administering to a mammal in need of such treatment and/or prevention, a therapeutically effective amount of a compound of Formulas 1–4 of the present invention.

The compounds of the present invention are also useful for the treatment of skin and muco-epithelial diseases in a mammal, such as psoriasis (in all its forms), lichen (including lichen planus), chronic eczema, icthyosis, pityriasis and chronic uticaria. Pharmaceutical compositions comprising a compound of Formulas 1–4 formulated for topical administration are particularly useful for the treatment of such skin and muco-epithelial diseases.

The present invention also provides methods of treatment and/or prevention of immunological disorders including organ transplantation rejection, graft versus host disease, psoriasis, autoimmune diseases, and chronic inflammatory diseases in a mammal comprising administering to the mammal in a therapeutically effective amount for the treatment of a desired aforesaid disease a combination of: (i) a compound of Formulas 1–4 as described below and (ii) at least one additional immunosuppressive agent. Such additional immunosuppressive agent may be selected from the group including but not limited to cyclosporin A (CSA or CsA) and analogs thereof, FK506 and analogs thereof, corticosteroids, azathioprine (AZA), mycophenolic acid or the 2-(N-morpholino)ethyl ester thereof, mycophenolate mofetil, rapamycin, 15-deoxyspergualin, mizoribine, leflunomide, OKT3, anti-interleukin-2 receptor antibodies, misoprostol, methotrexate, cyclophosphamide, and anti-lymphocyte/thymocyte serums.

The compounds of Formulas 1–4 of the present invention may also be administered in combination with a non-steroidal anti-inflammatory agent, selected from the group including but not limited to, aspirin, ibuprofen, naproxen, indomethacin, diclofenac, sulindac, piroxicam, etodolac, ketoprofen, meclofenamate, suprofen, and tolmetin, for the treatment and/or prevention of organ transplantation rejection, graft versus host disease, psoriasis, autoimmune diseases, and chronic inflammatory diseases in a mammal.

Compounds of Formulas 1–4 of the present invention may also be administered in combination with other tumor inhibiting agents, including but not limited to, 5-fluorouracil, for the treatment of tumors in a mammal.

The compounds of Formulas 1–4 of the present invention are potent inhibitors of dihydroorotate dehydrogenase, the fourth enzyme in the de novo pyrimidine nucleotide biosynthesis pathway.

Current recommended therapy for the prevention of organ transplantation rejection and related disorders, including graft versus host disease, traditionally involves patient treatment with cyclosporin A and adjunctive therapy with corticosteroids and other immunosuppressive drugs (Jacobs and Elgin, "Cyclosporin A, Current Status, Including the Cape Town Experience" in *Immune Modulation Agents and Their Mechanisms*, ISBN 0-8247-7178-8, 1984, pp 191–228; *Transplantation and Clinical Immunology*, Volume XX Combined Immuno-suppressive Therapy in Transplantation ISBN 0-444-81068-4, 1989). In view of the significant clinically observed toxicities associated with cyclosporin A (nephrotoxicity) and AZA (hepatoxicity), there is a need for improved therapies to replace or to be used in combination with cyclosporin A or AZA. The present results indicate that the compounds of Formulas 1–4 of the present invention will be useful as single therapy agents as well as agents to be used in combination with other compounds currently used in these clinical regimens such as cyclosporin A.

The compounds of Formulas 1–4 of the present invention have a unique mechanism of action (inhibition of dihydroorotate dehydrogenase) which is distinct from other available immunosuppressive agents. The compounds of Formulas 1–4 should be useful to permit the administration of reduced doses of other immunosuppressive agents (such as CsA and AZA) used in combination therewith, thereby reducing the adverse effects of these agents.

The isolation of FK506 is described in European Patent Application publication number 240,773, published Oct. 14, 1987 and the chemical synthesis of FK506 is described in Jones et al. (1989) *J. Am. Chem. Soc.* 111:1157–1159.

The preparation of azathioprine is described in U.S. Pat. No. 3,056,785 issued to Burroughs Wellcome. Azathioprine is available as Imuran®, for which the product information, including dosage and administration, is given in *Physicians' Desk Reference* 44th Edition, 1990, pp 777–778.

The preparation of cyclosporin A is described in U.S. Pat. No. 4,117,118 issued to Sandoz. Cyclosporin A is available as Sandimmune®, for which the product information, including dosage and information, is given in *Physicians' Desk Reference* 44th Edition, 1990, pp 1950–1952.

The preparation of prednisone is described in U.S. Pat. Nos. 2,897,216 and 3,134,718 issued to Schering. Prednisone is available commercially from several manufacturers as are other corticosteroids (see generally, *Physicians' Desk Reference*, supra).

Murine monoclonal antibody to the human T3 antigen (herein referred to as OKT3) is available as Orthoclone OKT®3, for which the product information, including dosage and administration and references to methods of preparation, is given in *Physicians' Desk Reference*, 1990, pp 1553–1554.

The preparation of mycophenolic acid is described in British patents 1,157,099; 1,157,100; and 1,158,387 issued to ICI.

15-Deoxyspergualin is a derivative of spergualin discovered in culture filtrates of the bacterial strain BGM162-aFZ as reported in Ochiai et al. Prolongation of Rat Heart Allograft Survival by 15-deoxyspergualin, *J. Antibiot* (Tokyo) 1987; 40:249.

Mizoribine is described in U.S. Pat. No. 3,888,843 issued to Toyo Jozo.

Misoprostol, a prostaglandin (PGE1) analog, is described in U.S. Pat. No. 3,965,143 assigned to Searle and U.S. Pat. No. 4,132,738 assigned to Miles.

Rapamycin is described in U.S. Pat. Nos. 4,650,803; 4,316,885; 4,885,171; 3,993,749 and 3,929,992, all assigned to Ayerst.

Antibodies to the IL-2 receptor protein are described in U.S. Pat. Nos. 4,578,335 and 4,845,198 (Immunex) and U.S. Ser. No. 7/341,361 and U.S. Pat. No. 4,892,827 issued to Pastan et al.

There is also provided by this invention methods of treating cancer in a mammal, including leukemia, lymphoma, and solid tumors, including pancreatic, mammary, colon, breast, lung, epithelial, and melanoma tumors, comprising the administration to a mammal bearing such a tumor a therapeutically effective tumor-inhibiting amount of a compound of Formulas 1–4 as described above.

The compounds of Formulas 1–4 of the present invention can be administered in combination with a second immunosuppressive agent, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent.

By "therapeutically effective amount" it is meant an amount of a compound of Formulas 1–4 that when administered alone or in combination with a second additional immunosuppressive agent to a cell or mammal is effective to prevent or ameliorate the disease condition or the progression of the disease.

By "administered in combination" or "combination" when referring to component (i) and component (ii) of the present invention, it is meant that the components are administered concurrently to the cell or mammal being treated. When administered in combination each component may be administered at the same time or sequentially in any order at different points in time. Thus, component (i) and component (ii) may be administered separately but sufficiently closely in time so as to provide the desired therapeutic effect.

This invention also includes pharmaceutical kits comprising or consisting essentially of: a pharmaceutical composition comprising a compound of Formulas 1–4; or a compound of Formulas 1–4 together with a pharmaceutical composition comprising at least one additional immunosuppressive agent. This invention also provides methods of using such pharmaceutical kits for the treatment of organ transplantation rejection, graft versus host disease, psoriasis and autoimmune diseases, including but not limited to rheumatoid arthritis, systemic lupus erythematous, multiple sclerosis, myasthenia gravis, insulin dependent diabetes, as well as chronic inflammatory disease including but not limited to Crohn's disease and primary biliary cirrhosis, in a mammal.

This invention also includes combination products comprising pharmaceutical compositions comprising a compound of Formulas 1–4 in physical combination or in a single dosage form with a second immunosuppressive agent, to pharmaceutical kits containing these combination products, and to methods of using these combination products for the treatment of organ transplantation rejection, graft versus host disease, psoriasis and autoimmune diseases, including but not limited to rheumatoid arthritis, systemic lupus erythematous, multiple sclerosis, insulin dependent diabetes, myasthenia gravis, as well as chronic inflammatory disease including but not limited to Crohn's disease and primary biliary cirrhosis, in a mammal.

The compounds of Formulas 1–4 herein described may have asymmetric centers. All chiral, diastereomeric, and racemic forms are included in the present invention. All chiral, diastereomeric, and racemic forms are intended for a given compound unless the specific stereochemistry for the compound is specifically indicated. All stable geometric isomers present in the compounds described herein are contemplated in the present invention and all geometric isomeric forms of a structure are intended, unless the specific isomer form is specifically indicated.

When any variable occurs more than one time in any constituent or in formula 1, 2, 3, or 4, or any other formula herein, its definition on each occurrence is independent of its definition at every other occurrence. Thus, for example, if a group is shown to be substituted with 0–3 $R^8$, then said group may optionally be substituted with up to three $R^8$ and $R^8$ at each occurrence is selected independently from the defined list of possible $R^8$. Also, combinations of substituents and/or variables are permissible only if such combinations result in stable compounds.

As used herein, "acyl of 1–4 carbons" is intended to include an alkyl group of 1–3 carbons attached through a carbonyl bridge (i.e. —C(=O)—($C_1$–$C_3$ alkyl)).

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "alkylthio" represents an alkyl group of indicated number of carbon atoms attached through an sulfur bridge; "alkylsulfinyl" represents an alkyl group of indicated number of carbon atoms attached through a sulfinyl bridge.

The term "substituted", as used herein, means that any one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds that are modified by making acid or base salts. Examples include, but are not limited to, mineral or organic acid salts of basic residues such as amines; and alkali or organic salts of acidic residues such as carboxylic acids.

Pharmaceutically acceptable salts of the compounds of this invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

SYNTHESIS

Compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

In the discussion below, compounds of Formula 1 are used in the schemes and accompanying text, and starting materials and intermediates appropriate to the preparation of compounds of Formula 1 are described. However, it is to be understood that the methods discussed are not limited to the preparation of compounds of Formula 1, but rather may be used for the preparation of compounds of Formulas 2, 3 and 4 as well, by substitution of the appropriate, analogous starting materials and intermediates. Although the structures shown in the schemes below are related to compounds of Formula 1, it will be understood that analogous schemes are applicable for the synthesis of compounds of Formulas 2, 3 and 4.

Compounds of Formulas 1, 2, 3 and 4 may be prepared by the reaction shown in Scheme 1 (which represents this reaction for the preparation of compounds of Formula 1). An appropriately substituted isatin of Formula 5 is condensed with an appropriately substituted cyclic ketone of Formula 6. This condensation, commonly called the Pfitzinger condensation, is well known in the chemical literature (for example, see Buu-Hoi et al., *J. Org. Chem.* (1953) 18:1209, and Jones, *Quinolines Part I*, 1977, Wiley, pp 197–207). The reaction is usually carried out in a suitable solvent, such as ethanol or a mixture of ethanol and water, in the presence of a suitable base, such as sodium hydroxide or potassium hydroxide, at a temperature in the range of about 5° C. to the boiling point of the solvent, preferably at the boiling point of the solve. Acidification of the reaction mixture with a mineral acid such as hydrochloric acid or an organic acid such as acetic acid provides the compounds of Formula 1, 2, 3, or 4. Alternatively, the compound of Formula 1, 2, 3, or 4 may be directly isolated from the reaction mixture as a salt, such as the sodium salt or potassium salt.

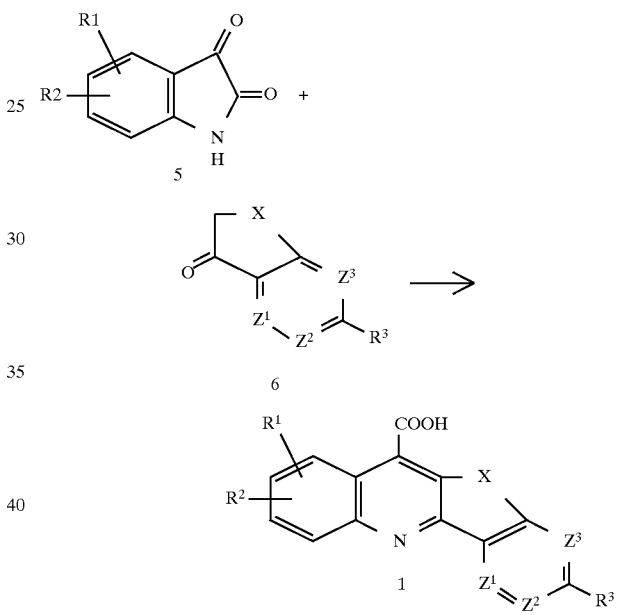

Scheme 1

Alternatively, compounds of Formulas 1, 2, 3 and 4 may be prepared by a two-reaction sequence as shown in Scheme 2 (which represents this reaction sequence for the preparation of compounds of Formula 1). This alternative two-reaction sequence is preferred when the ketone of Formula 6 is unstable to the reaction conditions required for the reaction of Scheme 1, or is unreactive under these conditions. In this alternative reaction sequence, an appropriately substituted isatin of Formula 5 is reacted with an appropriately substituted cyclic ketone of Formula 6, in a suitable solvent such as ethanol, in the presence of a suitable base such as diethylamine or pyrrolidine, at a temperature in the range of about 5° C. to the boiling point of the solvent, to provide an intermediate aldol condensation product of Formula 7. The product of Formula 7 is then reacted further in a suitable solvent such as ethylene glycol dimethyl ether or dioxane, in the presence of a mineral acid such as aqueous hydrochloric acid or an organic acid such as methanesulfonic acid, in an amount which represents about 25–100% of the volume of the solvent. The temperature of the reaction is in the range of about 5° C. to the boiling point of the solvent. Removal of the solvent and treatment with water provides the compound of Formula 1, 2, 3, or 4.

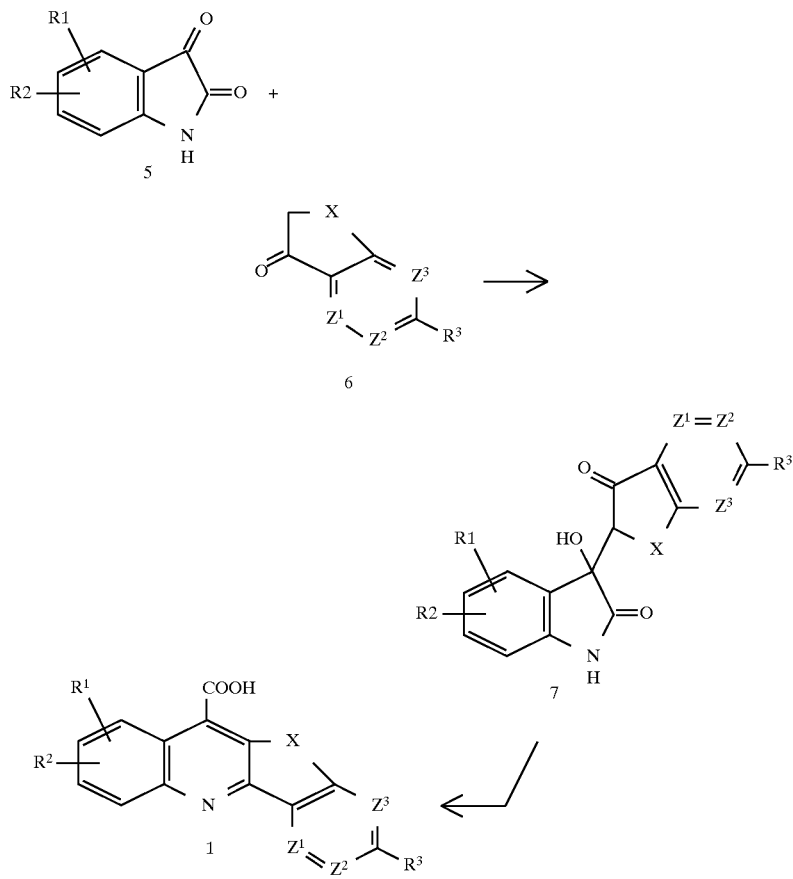

Scheme 2

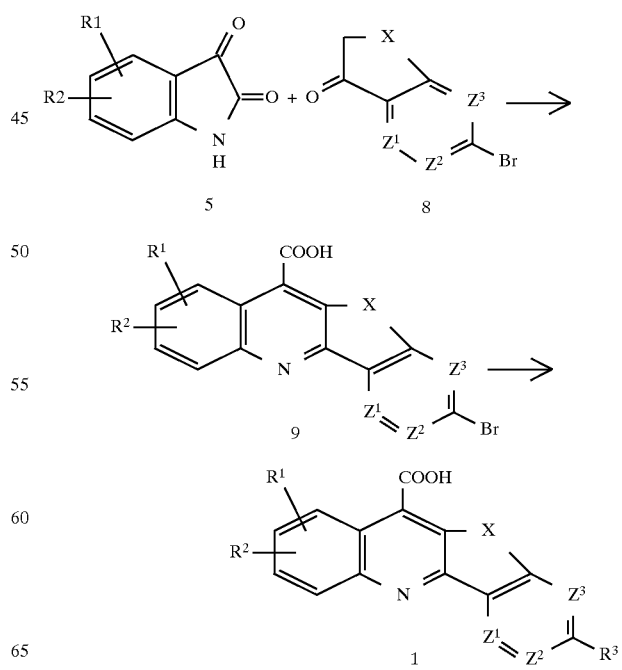

Scheme 3

Alternatively, the compounds of Formulas 1, 2, 3 and 4 where $R^3$ is phenyl, furyl, thienyl, pyridyl, thiazolyl, or oxazolyl (wherein said phenyl, furyl, thienyl, pyridyl, thiazolyl, or oxazolyl is optionally substituted) may be prepared according to the reaction sequence shown in Scheme 3 (which represents this reaction sequence for the preparation of compounds of Formula 1). In this sequence, a ketone of Formula 8 (where the $R^3$ substituent of the ketone of Formula 6 has been replaced by an appropriate substituent such as bromo) is condensed with an isatin of Formula 5, using the Pfitzinger condensation analogous to that shown in Scheme 1 or the two-step reaction sequence analogous to that shown in Scheme 2, to provide the compound of Formula 9. This compound is then coupled with an arylboronic acid or heteroarylboronic acid $R^3$—B(OH)$_2$ using a standard coupling reaction such as that described by Miyara et al. [*Synth. Comm.* (1981) 11:513], commonly referred to as a Suzuki coupling, to provide the compound of Formula 1, 2, 3, or 4. The use of this reaction sequence requires that $R^1$ and $R^2$ are not Br.

Certain substituents on compounds of Formulas 5 and/or 6 may be incompatible with the reaction conditions to prepare the compounds of Formulas 1, 2, 3 or 4. In these cases, the substituents may be replaced with suitable protected forms of the desired substituents, or with suitable precursors to the desired substituents. After isolation of the product of the reaction sequences shown in Schemes 1, 2 or 3, the desired substituents may be elaborated by suitable deprotection or other manipulations to provide the compound of Formula 1, 2, 3 or 4. Cases where this may be necessary will be evident to one skilled in the art, as will the methods to be used for conversion to the desired compounds.

Compounds of Formulas 1, 2, 3 and 4 wherein X is $CR^5=CR^6$, $CR^6=N$ or $N=CR^6$ may be prepared from the corresponding compounds where X is $CHR^5CHR^6$, $CHR^6NH$ or $NHCHR^6$, respectively, by methods well known in the art. Examples are treatment with 2,3-dichloro-5,6-dicyano-1,4-benzoquinone in a solvent such as benzene or toluene, as described by Pataki et al. [i J. Org. Chem. (1987) 52:2226], and treatment with palladium on charcoal as described by Garrett et al. [*Tetrahedron Lett.* (1969) 191].

Compounds of Formula 1, 2, 3, or 4 which contain an acyl group as $R^4$ and/or $R^7$ may be prepared from the corresponding compound where $R^4$ and/or $R^7$ is H, using methods well known in the art, such as acylation with an acid chloride or anhydride.

Isatins of Formula 5 used as starting materials for the compounds of Formula 1, 2, 3 and 4 are either commercially available, or may be prepared using methods as described by Papp and references given therein [*Adv. Heterocyclic Chem.* (1975) 18:1].

Ketones of Formula 6 (which may be used to prepare compounds of Formula 1, and which in the following discussions are meant to represent also the ketones which may be used to prepare compounds of Formulas 2, 3, and 4) may be prepared using a variety of standard methods well known in the literature. Several applicable methods are herein described, but these methods are meant as illustrative examples only and do not constitute a limitation to the present invention.

In cases of suitable reactivity which will be apparent to one skilled in the art, the ketones of Formula 6 may be prepared by a Friedel-Crafts acylation reaction as illustrated in Scheme 4. A suitable carboxylic acid precursor of Formula 10 may either be cyclized directly to 6 using an acid catalyst such as sulfuric acid, methanesulfonic acid, or polyphosphoric acid, optionally in an appropriate solvent, or the acid may first be activated by conversion to the corresponding acid chloride or acid anhydride using standard methods, after which it may be cyclized by use of an appropriate Lewis acid catalyst such as aluminum chloride or boron trifluoride, in an appropriate solvent. The Friedel-Crafts acylation reaction is well known in the chemical literature, and has been extensively reviewed, for example by Gore [Chapter 31 in Olah, *Friedel-Crafts and Related Reactions*, vol. 3, 1964, Interscience Publishers]. This method will be limited to cases in which the ring onto which the acylation is to occur is sufficiently reactive toward Friedel-Crafts acylation conditions, such as for example a benzene or thiophene ring. The carboxylic acids of Formula 10 may in turn be prepared using reactions and methods well known in the chemical literature.

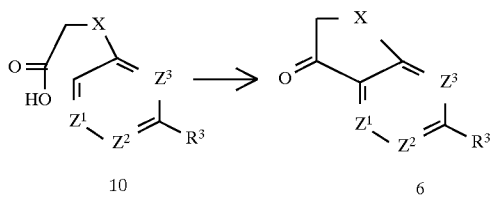

Ketones of Formula 6 may also be prepared using the reaction sequence shown in Scheme 5. A suitable starting material of Formula 11, where $G^1$ and $G^2$ are suitable functional groups such as carboxylate esters, nitrites, or carboxylic acids, may be cyclized using conditions appropriate to the substituents $G^1$ and $G^2$ to give an intermediate of Formula 12, which may then be further converted to the ketone of Formula 6. In the case where $G^1$ and $G^2$ are carboxylate esters, the cyclization is commonly known as the Dieckmann condensation. In the case where $G^1$ and $G^2$ are nitriles, the cyclization is commonly known as the Thorpe-Ziegler condensation. These reactions are well known in the chemical literature (see, for example, Schaefer et al. [*Org. Reactions* (1967) 15:1]), and may be carried out in an appropriate solvent using a basic catalyst, such as sodium methoxide, sodium ethoxide, or potassium t-butoxide. In the case where $G^1$ and $G^2$ are carboxylic acids, the reaction may be carried out by treatment with acetic anhydride and acetic acid, according to the procedure of Normant-Chefnay et al. [*Compt. Rend. Acad. Sci. (C)* (1968) 267:547]. The cyclized intermediate of Formula 12 may then be further reacted under appropriate conditions to cause removal of the group $G^2$, providing the desired ketone of Formula 6. Such conditions are well known in the chemical literature, and usually involve acid- or base-catalyzed hydrolysis of a nitrile or an ester to the corresponding carboxylic acid, which is then decarboxylated using well-known methods to provide the compound of Formula 6. In the case where $G^1$ and $G^2$ are carboxylic acids, the intermediate compound of Formula 12 is not isolated, but undergoes decarboxylation in the reaction to provide the compound of Formula 6 directly.

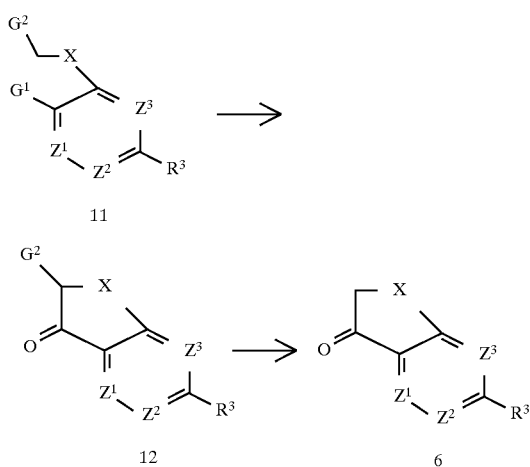

Ketones of Formula 6 wherein X is $CH_2O$ or $CH_2S$ may also be prepared by the reaction sequence shown in Scheme 6. An appropriate methyl ketone of Formula 13, where Y is O or S, may be converted to a compound of Formula 14, where the wavy line represents either a single or double bond, and where either R is an alkyl group such as methyl or ethyl, or $NR^2$ is a cyclic amino group such as pyrrolidine, piperidine, or morpholine. In the case where the wavy line is a single bond, this reaction is called the Mannich reaction, and is very well known in the chemical literature (see, for example, Blicke [*Org. Reactions* (1942) 1:303, and Cox et al. [*Synthesis* (1989) 709]). In the case where the wavy line is a double bond, this reaction may be achieved, for example, by condensation of 13 with a compound such as N,N-dimethylformamide dimethyl acetal, as reported by Lin et al. [*J. Heterocyclic Chem.* (1977) 14:345]. In some cases, the compound of Formula 14 may spontaneously cyclize to provide the desired compound of Formula 15 (which is equivalent to the ketones of Formula 6 where X is $CH_2O$ or $CH_2S$), while in other cases the cyclization may be induced by treatment with an appropriate reagent, such as an acidic or a basic catalyst. In the case where the wavy bond of 14 is a double bond, then the keto ring of 15 will contain a double bond, which may be reduced using standard methods known in the literature to provide the desired compound of Formula 15.

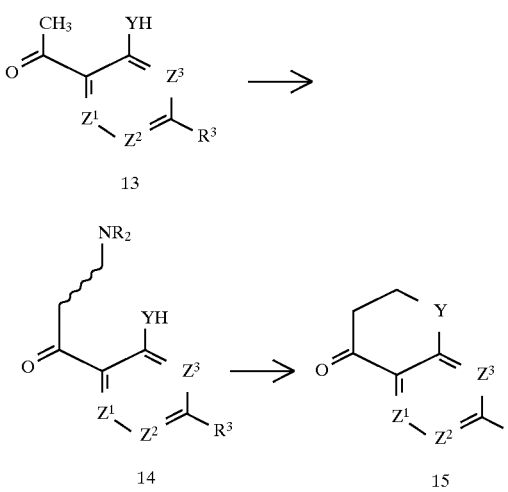

In cases where $R^3$ is phenyl, furyl, thienyl, pyridyl, thiazolyl, or oxazolyl (wherein said phenyl, furyl, thienyl, pyridyl, thiazolyl, or oxazolyl is optionally substituted), ketones of structure 6 may also be synthesized from a suitable precursor ketone 16, where G is bromo or hydroxy, by a coupling reaction with an arylboronic acid or a heteroarylboronic acid as shown in Scheme 7. In the case where G is bromo, the coupling reaction may be performed using the Suzuki coupling mentioned earlier, in reference to Scheme 3. Alternatively, in the case where G is hydroxy, the hydroxy group may be activated by conversion to the corresponding trifluoromethanesulfonate, using standard methods and techniques. The resulting trifluoromethanesulfonate may be coupled with an arylboronic acid or heteroarylboronic acid, for example using the procedure described by Oh-e et al. [*Synlett* (1990) 221].

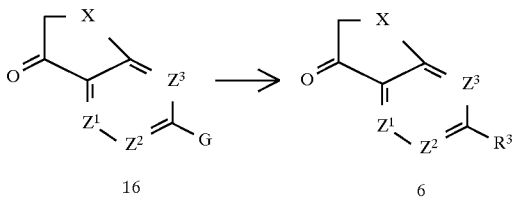

Examples of the preparation of ketone starting materials of Formula 6 and related ketones which may be used to synthesize compounds of Formulas 1, 2, 3, and 4 are given below.

All melting points are uncorrected. All reactions were conducted under a nitrogen atmosphere except where otherwise noted. All commercial chemicals were used as received. Chromatography was performed with Merck silica gel 60 (230–400 mesh). The chromatography eluents are given as ratios by volume. Organic phases from solvent-solvent extractions were generally dried over magnesium sulfate, unless otherwise noted. Solvents were generally removed by evaporation under reduced pressure on a rotary evaporator unless otherwise noted. Peak positions for $^1H$ NMR spectra are reported as parts per million (δ) downfield from the internal standard tetramethylsilane. Abbreviations for $^1H$ NMR spectra are as follows: s=singlet, d=doublet, m=multiplet, dd=doublet of doublets, dm=doublet of multiplets. Mass spectra were obtained using chemical ionization with ammonia as the reagent gas.

Preparation of 6-(4-methylphenyl)-1-tetralone a. 6-Methoxytetralone (50 g, 280 mmol) was suspended in glacial acetic acid (250 mL). Hydrobromic acid (47%; 500 mL) was added and the mixture was heated at reflux for 6 h, cooled to room temperature, and poured onto 500 g of crushed ice. After 1 h the precipitate was collected and recrystallized from ethanol to provide 32 g of 6-hydroxytetralone. Concentration of the mother liquor provided an additional 9 g of product, mp 149°–152° C.; $^1H$ NMR ($CDCl_3$) δ7.80 (d, 1H), 6.78 (d, 1H), 6.68 (s, 1H), 2.90 (t, 2H), 2.55 (t, 2H), 2.05 (m, 2H).

b. A portion of the product of part a (9.0 g, 55.5 mmol) was dissolved in dimethoxyethane (100 mL). Pulverized potassium carbonate (16.88 g, 122 mmol) was added and the reaction mixture heated at reflux under nitrogen for 10 minutes, then cooled to room temperature. N-Phenyltrifluoromethanesulfonimide (19.85 g, 55.5 mmol) was added and the mixture heated at reflux for 0.5 h, then cooled to room temperature. The solvent was decanted from the solid, which was washed with additional dimethoxyethane. The washings were added to the decanted solution and the combined solvents evaporated to yield an oil. Purification by column chromatography on silica gel using 5:1 hexane/ethyl acetate as eluant provided 15.7 g (96%) of 6-trifluoromethanesulfonyloxy-1-tetralone as an off-white solid; $^1H$ NMR ($CDCl_3$) δ8.15 (d, 1H), 7.25–7.15 (m, 2H), 3.02 (t, 2H), 2.65 (t, 2H), 2.18 (m, 2H).

c. A portion of the product of part b (8.0 g, 27.2 mmol), 4-methylphenylboronic acid (4.07 g, 29.9 mmol), and pulverized tribasic potassium phosphate (8.65 g, 40.7 mmol) were suspended in anhydrous dioxane. The reaction mixture was degassed by bubbling nitrogen through the suspension for 10 minutes. Tetrakis(triphenylphosphine)palladium (943 mg, 0.8 mmol) was added and the mixture was heated at reflux for 5 h, allowed to cool to room temperature, diluted with diethyl ether, filtered and evaporated. Purification by chromatography on silica gel using dichloromethane as eluant provided 2.2 g (34%) of 6-(4-methylphenyl)-1-tetralone as an off-white solid; $^1$H NMR (CDCl$_3$) δ8.05 (d, 1H), 7.58–7.25 (m, 6H), 3.05 (t, 2H), 2.64 (t, 2H), 2.40 (s, 3H); Mass spectrum (methane chemical ionization) m/z 265 (M+C$_2$H$_5$), 237 (M+H).

Preparation of 2-phenyl-7,8-dihydroquinolin-5(6H)-one

3-Aminocyclohexenone (5.55 g, 50 mmol) and 3-dimethylaminopropiophenone hydrochloride (10.65 g, 50 mmol) were suspended in glacial acetic acid (15 mL) and heated at reflux for 1 h. The mixture was cooled to room temperature and cautiously poured into 20% aqueous sodium carbonate. After gas evolution ceased the residue was extracted with chloroform, dried over anhydrous sodium carbonate, filtered and evaporated. Purification by chromatography on silica gel using 1:1 chloroform/dichloromethane as eluant provided 2.95 g (26%) of 2-phenyl-7,8-dihydroquinolin-5(6H)-one as an off-white solid, mp 128°–130 ° C.; $^1$H NMR (CDCl$_3$) δ8.32 (d, 1H), 8.05 (dd, 2H), 7.66 (d, 2H), 7.55–7.42 (m,3H), 3.21 (t, 2H), 2.72 (t, 2H), 2.22 (m, 2H).

Preparation of 2-phenyl-7,8-dihydro-1,3-quinazolin-5(6H)-one a. 1,3-Cyclohexanedione (11.2 g, 100 mmol) was suspended in dimethylformamide dimethylacetal (28 mL) and the mixture was heated at reflux for 1 h. The mixture was cooled to room temperature and the solvent was evaporated to provide an orange solid, which was recrystallized from ethyl acetate to provide 12 g (72%) of 2-dimethylaminomethylene-1,3-cyclohexanedione as light orange needles, mp 116°–118° C.; $^1$H NMR (CDCl$_3$) δ8.05 (s, 1H), 3.40 (s, 3H), 3.19 (s, 3H), 2.26 (t, 4H), 1.95 (m, 1H).

b. Sodium (1.09 g 47 mmol) was cautiously added in small portions to anhydrous ethanol over 15 minutes, and the mixture was stirred until all of the sodium dissolved. Benzamidine hydrochloride (7.80 g, 49 mmol) was added, followed by a portion of the material from part a (8.31 g, 50 mmol) dissolved in ethanol (30 mL). The mixture was heated at reflux for 1 h and cooled to room temperature. The solvent was evaporated and the residue treated with water (100 mL), and the product filtered. The product was recrystallized from ethyl acetate to provide 5.2 g (42%) of 2-phenyl-7,8-dihydro-1,3-quinazolin-5(6H)-one as light yellow cubes, mp 122°–124° C.; $^1$H NMR (CDCl$_3$) δ9.25 (s, 1H), 8.55 (dd, 2H), 7.58–7.48 (m, 3H), 3.18 (t, 2H), 2.74 (t, 2H), 2.24 (m, 2H); Mass spectrum m/z 225 (M+H).

Preparation of 7-phenylthiochroman-4-one a. 3-Bromothiophenol (10 g, 52.9 mmmol) was dissolved in acrylonitrile (11.28 g, 213 mmol). Triton B (1 mL) was added, at which time the reaction mixture became exothermic and began to reflux without added heat. The mixture was allowed to cool to room temperature, poured into cold aqueous sodium hydroxide (2%; 200 mL), and extracted with diethyl ether. The organic layer was dried, filtered and evaporated to provide 12 g (93%) of 3-[(3-bromophenyl)thio]propionitrile as a tan oil; $^1$H NMR (CDCl$_3$) δ7.54 (s, 1H), 7.42 (d, 1H), 7.32 (d, 1H), 7.25–7.15 (m, 2H), 3.15 (t, 2H), 2.62 (t, 2H); Mass spectrum m/z 261, 259 (M+NH$_4$).

b. The product of part a (12.0 g, 50 mmol) was dissolved in glacial acetic acid (10 mL). Concentrated hydrochloric acid (250 mL) was added and the reaction mixture was heated at reflux for 4 h. The mixture was cooled to room temperature and poured onto 250 g of crushed ice. After the ice melted the precipitate was filtered and dissolved in a saturated aqueous solution of sodium bicarbonate (250 mL), and the solution was washed with ethyl acetate. The aqueous layer was cautiously acidified with concentrated hydrochloric acid and extracted with ethyl acetate The organic phase was dried, filtered and evaporated to provide 7.4 g (54%) of 3-[(3-bromophenyl)thio]propanoic acid as a white powder, mp 87°–88° C. $^1$H NMR (DMSO-d$_6$) δ7.52 (s, 1H), 7.40–7.25 (m, 3H), 3.18 (t, 2H), 2.53 (t, 2H); Mass spectrum m/z 280, 278 (M+NH$_4$), 262, 260 (m+H).

c. A portion of the product of part b (2.61 g, 10 mmol) was pulverized and added to concentrated sulfuric acid (8 mL), and the mixture was stirred at room temperature for 3 h. The mixture was poured onto ice. After the ice melted the mixture was extracted with ethyl acetate. The organic extract was cautiously washed with a saturated aqueous solution of sodium bicarbonate, then with brine. The organic phase was dried, filtered and evaporated. The product was recrystallized from benzene/hexane to provide 1.6 g (66%) of 7-bromothiochroman-4-one as a white powder, mp 55°–57° C.; $^1$H NMR (CDCl$_3$) δ7.94 (d, 1H), 7.45 (s, 1H), 7.30 (dd 1H), 3.25 (t, 2H), 2.97 (t, 2H); Mass spectrum m/z 262, 260 (M+NH$_4$), 245, 243 (M+H).

d. The product of part c (15.00 g, 61.47 mmol), phenylboronic acid (7.52 g, 61.67 mmol), and tetrabutylammonium bromide (0.99 g, 3.07 mmol) were dissolved in toluene (200 mL), aqueous sodium carbonate (2M; 60 mL) and ethanol (30 mL). The mixture was degassed by passing a stream of nitrogen through the vigorously stirred mixture for 0.5 h. Tetrakis(triphenylphosphine)palladium (2.14 g, 1.8 mmol) was added and the mixture was heated at reflux overnight (approx 16 h). The mixture was cooled to room temperature, and the layers separated. The aqueous layer was extracted with ethyl acetate (2×50 mL). The combined organic layers were dried, filtered through a plug of silica gel, and evaporated to a white solid which was recrystallized from benzene/hexane to provide 10.9 g (74%) of 7-phenylthiochroman-4-one as an off-white powder, mp 85°–87 ° C.; $^1$H NMR (CDCl$_3$) δ8.17 (d, 1H), 7.60–7.36 (m, 7H), 3.24 (t, 2H), 2.98 (t, 2H); Mass spectrum m/z 258 (M+NH$_4$) 241 (M+H).

Preparation of 7-(4-methylphenyl)chroman-4-one a. 3-Bromophenol (100 g, 580 mmol) and triethylamine (104 mL, 750 mmol) were dissolved in dichloromethane (500 mL), and the solution was cooled in an ice bath. Acetyl chloride (49.7 g, 630 mmol) was added dropwise. After 1 h the cooling bath was removed and the mixture was stirred overnight (approx 16 h) at room temperature. The mixture was washed with hydrochloric acid (1N, 250 mL), water (250 mL), 5% NaHCO$_3$ (250 mL), and brine (250 mL). The organic layer was dried and evaporated to provide 124 g (99%) of 3-bromophenyl acetate as a light brown liquid; $^1$H NMR (CDCl$_3$) δ7.36 (d, 1H), 7.32–7.20 (m, 2H), 7.05 (d, 1H), 2.28 (s, 3H).

b. The product of part a (60 g, 280 mmol) was added to aluminum chloride (120 g, 890 mmol) and placed in an oil bath at 160° C. for 3 h. The mixture was allowed to cool to room temperature and poured onto 300 g of an ice/hydrochloric acid (1N) mixture. After the ice melted the mixture was extracted with ethyl acetate. The organic layer was dried, filtered through a pad of silica gel and evaporated to yield a light yellow oil which solidified under vacuum to provide 53 g (88%) of 4-bromo-2-hydroxyacetophenone; $^1$H NMR (CDCl$_3$) δ12.32 (s, 1H), 7.58 (d, 1H), 7.18 (s, 1H), 7.05 (d, 1H), 3.60 (s, 3H).

c. The product of part b (53 g, 250 mmol) was dissolved in dimethylformamide dimethyl acetal (98 mL) and heated at reflux under nitrogen for 1 h, during which time a precipitate formed. The mixture was cooled to room temperature, glacial acetic acid (100 mL) was cautiously added and the mixture was heated at reflux for 1 h. Analysis of an aliquot of the reaction mixture by thin-layer chromatography and $^1$H NMR showed the reaction had not gone to completion, so additional acetic acid (100 mL) was added and the mixture was refluxed for an additional 2 h, and allowed to stand at room temperature overnight (approx 16 h). The precipitate was filtered, dried and recrystallized from ethanol to provide 37 g (68%) of 7-bromochromen-4-one. Concentration of the mother liquor provided an additional 12 g of product, mp 154°–155° C.; $^1$H NMR (CDCl$_3$) δ8.05 (d, 1H), 7.82 (d, 1H), 7.62 (s, 1H), 7.55 (d, 1H), 6.35 (d, 1H); Mass spectrum m/z 244, 242 (M+NH$_4$), 225, 227 (M+H).

d. The product of part c (4.5 g, 20 mmol), 4-methylphenylboronic acid (3.26 g, 24 mmol) and tetrabutylammonium bromide (322 mg, 1 mmol) were dissolved in a mixture of toluene (40 mL), ethyl alcohol (10 mL) and 2M aqueous sodium carbonate, and degassed by passing a stream of nitrogen through the vigorously stirred mixture for 0.5 h. Tetrakis(triphenylphosphine)palladium (139 mg, 0.12 mmol) was added and the mixture was heated at reflux overnight (approx 16h.). The mixture was cooled to room temperature and filtered through celite. The layers were separated and the aqueous layer was extracted with ethyl acetate. The combined organic layers were filtered through a pad of silica gel and evaporated to provide 3.2 g (68%) of 7-(4-methylphenyl)chromen-4-one as a light tan powder, mp 159°–160° C.; $^1$H NMR (CDCl$_3$) δ8.35 (d, 1H), 7.95 (d, 1H), 7.72 (m, 1H), 7.65 (d, 2H), 7.38 (d, 2H), 6.42 (d, 1H), 2.50 (s, 3H); Mass spectrum m/z 237 (M+H).

e. The product of part d (1.80 g, 7.62 mmol) was dissolved in anhydrous tetrahydrofuran (100 mL) and cooled in a dry ice-acetone bath. Potassium tri-sec-butylborohydride, (1.0M in tetrahydrofuran; 7.6 mL, 7.6 mmol) was added dropwise and the mixture was stirred for 1 h, at the cooling bath temperature. The reaction mixture was poured into a 20% aqueous solution of monobasic potassium phosphate, and extracted with ethyl acetate. The organic layer was dried, filtered and evaporated. Purification by column chromatography on silica gel using 1:1 chloroform/dichloromethane provided 1.46 g (81%) of 7-(4-methylphenyl)chroman-4-one as an off-white solid; $^1$H NMR (CDCl$_3$) δ7.85 (d, 1H), 7.52 (d, 2H), 7.35–7.18 (m, 4H), 4.58 (t, 2H), 2.82 (t, 2H), 2.40 (s, 3H).

Preparation of 7-phenylisochroman-4-one a. Methyl iodide (10.0 mL, 160 mmol) was added to a mixture of 4-bromo-2-methylbenzoic acid (25.0 g, 116 mmol) and potassium carbonate (20.0 g, 145 mmol) in anhydrous dimethylformamide (75 mL) at room temperature under a nitrogen atmosphere and stirred for 18 h. The mixture was poured into water and extracted with ethyl acetate (3×50 mL). The organic phases were combined, washed with copper sulfate solution (50 mL) and brine (50 mL), dried and evaporated. Purification by column chromatography on silica gel using 9:1 hexane/ethyl acetate as eluant provided 21.0 g (79%) of methyl 4-bromo-2-methylbenzoate as a clear liquid: $^1$H NMR (CDCl$_3$) δ7.85 (d, 1H), 7.42–7.47 (m, 2H), 3.95 (s, 3H), 2.64 (s, 3H); IR (neat) 1726 cm$^1$; Mass spectrum m/z 197, 199 (M+H–OCH$_3$).

b. A mixture of the product of part a (20.0 g, 87 mmol), N-bromosuccinimide (15.54 g, 87 mmol), and benzoyl peroxide (0.21 g, 1 mole %) in carbon tetrachloride (75 mL) was heated to reflux under a nitrogen atmosphere for 3 h. The solution was cooled to room temperature and filtered. The filtrate was concentrated to give an orange oil which formed crystals upon standing. A white solid was collected by suction filtration and recrystallized from hexane to provide 15.23 g (56%) of methyl 2-bromomethyl-4-bromobenzoate as a white powder, mp 78°–79° C.: $^1$H NMR (CDCl$_3$) δ7.84 (d, 1H), 7.63 (s, 1H), 7.50(d of d, 1H), 4.89 (s, 2H), 3.94 (s, 3H); IR (KBr) 1722 cm$^1$; Mass spectrum m/z 325 (M+NH$_4$); Anal. calcd. for C$_9$H$_8$Br$_2$O$_2$: C 35.10, H 2.62, Br 51.89; Found: C 35.09, H 2.63, Br 51.67.

c. Sodium hydride (1.43 g; 60% in oil, 36 mmol) was suspended in anhydrous tetrahydrofuran (10 mL) under a nitrogen atmosphere. A solution of the product of part b (10.0 g, 32 mmol) and methyl glycolate (2.76 mL, 36 mmol) in anhydrous tetrahydrofuran (40 mL) was added at room temperature and the mixture was heated at reflux for 3 h. After cooling to room temperature, the solution was quenched with methanol (2 mL), poured into water (200 mL), and extracted with ethyl acetate (50 mL). The organic phase was washed with brine, dried and evaporated to give a white residue. Purification by column chromatography on silica gel using 4:1 hexane/ethyl acetate as eluant provided 7.10 g (69%) of methyl 2-[(2-methoxy-2-oxoethoxy)methyl]-4-bromobenzoate as a white solid, mp 60°–62° C.: $^1$H NMR (CDCl$_3$) δ7.93 (s, 1H), 7.83 (d, 1H), 7.48 (dd, 1H), 5.01 (s, 2H), 4.25 (s, 2H), 3.88 (s, 3H), 3.79 (s, 3H); IR (KBr) 1758, 1720 cm$^1$; Mass spectrum m/z 334 (M+NH$_4$); Anal. calcd. for C$_{12}$H$_{13}$BrO$_5$: C 45.45, H 4.13, Br 25.20; Found: C 45.42, H 4.03, Br 25.17.

d. A mixture of the product of part c (6.77 g, 21 mmol) and sodium hydroxide (50% aqueous solution, excess) in 50% aqueous ethanol (200 mL) was heated at reflux for 5 h. The solution was cooled to room temperature, poured into water (400 mL), and acidified with concentrated hydrochloric acid to give a white precipitate which was collected by filtration and air dried to provide 6.04 g (98%) of 2-[(2-hydroxy-2-oxoethoxy)methyl]-4-bromobenzoic acid as a white solid, mp 194°–196° C.: $^1$H NMR (DMSO-d$_6$) δ7.84 (m, 2H), 7.62 (d, 1H), 4.90 (s, 2H), 4.19 (s, 2H); IR (KBr) 1704 cm$^1$; Mass spectrum m/z 230 (M—CH$_2$COOH); Anal. calcd. for C$_{10}$H$_9$O$_5$Br: C 41.55, H 3.14, Br 27.64; Found: C 41,33, H 3.08, Br 27.42.

e. A mixture of the product of part d (5.48 g, 19 mmol) and potassium acetate (3.0 g, 31 mmol) in acetic anhydride (10.0 mL) was heated at reflux under a nitrogen atmosphere for 18 h. The reaction solution was cooled to room temperature and concentrated. Aqueous sodium hydroxide (1N; 100 mL) was added carefully, and the aqueous solution was extracted with diethyl ether (3×50 mL). The organic extracts were combined, dried and evaporated. The residue was taken up in aqueous sodium hydroxide (1N; 100 mL) and stirred for 5 min at room temperature. The mixture was poured into water (400 mL) and the solid was collected by filtration. Purification by column chromatography on silica gel using 5:1 hexane/ethyl acetate as eluant provided 1.15 g (27%) of 7-bromoisochroman-4-one as a white solid, mp 144°–146 ° C.: $^1$H NMR (CDCl$_3$) δ7.91 (d, 1H), 7.57 (dd, 1H), 7.41 (s, 1H), 4.86 (s, 2H), 4.36 (s, 2H); IR (KBr) 1688 cm$^1$; Mass spectrum m/z 226 (M+H); Anal. calcd. for C$_9$H$_7$O$_2$Br: C 47.61, H 3.11, Br 35.19; Found: C 47.65, H 3.10, Br 35.04.

f. Nitrogen gas was bubbled through a mixture of the product of part e (0.611 g, 27 mmol) and phenylboric acid (0.36 g, 29 mmol) in 5:2 toluene/ethanol (30 mL) for 4 hours. Sodium carbonate (0.57 g, 5.38 mmol) was added followed by tetrabutylammonium bromide (0.049 g, 0.13 mmol) and tetrakis(triphenylphosphine)palladium (0.012 g, 0.04 mmol). The solution was heated at reflux for 18 h, cooled to room temperature, and evaporated. The residue was taken up in water (50 mL) and extracted with ethyl acetate (3×20 mL). The organics were combined, washed with brine, dried and evaporated. The solid was recrystallized from hexane to provide 0.429 g (70%) of 7-phenylisochroman-4-one as a gold-colored solid, mp 127°–128 ° C.: $^1$H NMR (CDCl$_3$) δ8.12 (d, 1H), 7.60–7.66 (m, 3H), 7.39–7.51 (m, 4H), 4.96 (s, 2H), 4.41 (s, 2H); IR (KBr) 1688 cm$^1$; Mass spectrum m/z=225 (M+H); Anal. calcd. for $C_{15}H_{12}O_2$: C 80.34, H 5.39; Found: C 80.03, H 5.45.

Preparation of 7-phenylisothiochroman-4-one a. To a solution of 3-bromobenzyl bromide (23.75 g, 90 mmol) and thioglycolic acid (11.42 g, 120 mmol) in ethanol (150 mL) was added potassium hydroxide (14.24 g, 250 mmol) in water (50 mL). The reaction was heated at reflux for 3.5 h, cooled and the ethanol was evaporated. The residue was quenched with water (100 mL) and the mixture was extracted with ether (50 mL). The aqueous layer was acidified to pH 1 with concentrated hydrochloric acid, extracted with ethyl acetate (2×100 mL) and the organic phase was dried. Evaporation of the solvent followed by washing of the residue with hexane afforded 3-bromophenylmethylthioacetic acid as a white solid (92%), mp 90°–91 ° C.: $^1$H NMR (CDCl$_3$) δ3.10 (s, 2H), 3.82 (s, 2H), 7.20–7.29 (m, 2H), 7.39–7.42 (dd, 1H), 7.52 (d, 1H); IR (KBr) 1706 cm$^{-1}$; Mass spectrum m/z 280 (M+NH$_4$); Anal. calcd. for $C_9H_9O_2SBr$: C 41,39, H 3.47, S 12.28; Found C 41.43, H 3.49, S 12.10.

b. To a cold (0° C.) solution of the product of part a (22.00 g, 80 mmol) in methylene chloride (200 mL) was added oxalyl chloride (11.81 g, 90 mmol) dropwise followed by four drops of dimethylformamide. The reaction mixture was stirred vigorously at 0° C. and then at room temperature for 5 h. The mixture was concentrated to a yellow oil which was redissolved in fresh methylene chloride (100 ml). The solution was added dropwise at 0° C. to a slurry of aluminum chloride (11.30 g, 80 mmol) in methylene chloride (150 mL). The mixture was warmed to room temperature and stirred for 48 h, then was poured into crushed ice (150 g). The organic layer was separated and washed with water (50 mL), saturated sodium bicarbonate (50 mL) and brine (50 mL), dried and evaporated to a dark brown solid. Chromatography on silica gel using 20:1 hexane:ethyl acetate as eluant afforded 7-bromoisothiochroman-4-one (88%) as a brown solid, mp 81° C.; $^1$H NMR (CDCl$_3$) δ3.54 (s, 2H), 3.88 (s, 2H), 7.26 (s, 1H), 7.50 (d, 1H), 7.95 (d, 1H); IR (KBr) 1676 cm$^1$; Mass spectrum m/z 245 (M+H); Anal. calcd. for $C_9H_7BrOS$: C 44.46, H 2.90, S 13.19; Found C 44.28, H, 2.77, S 13.09.

c. 7-Phenylisothiochroman-4-one was prepared in 62% yield via the procedure used in part f of the preparation of 7-phenylisochroman-4-one, and was recrystallized from benzene/hexanes, mp 87°–89° C.: $^1$H NMR (CDCl$_3$) δ3.59 (s, 2H), 3.99 (s, 2H), 7.38–7.47 (m, 4H), 7.49–7.60 (m, 3H), 8.17 (d, 1H); IR (KBr) 1674, cm$^{-1}$; Mass spectrum m/z 241 (100); Anal. calcd. for $C_{15}H_{12}O_5$: C 74.97, H 5.03, S 13.34; Found C 75.06, H 5.00, S 13.20.

Preparation of 7-phenyl-8-aza-isothiochroman-4-one

To a solution of ethyl 2-methyl-6-phenylnicotinate (prepared according to Spath et al. [*Monatsh. Chem.* (1928) 49:265]) (1.00 g, 4.10 mmol) in carbon tetrachloride (10 mL) was added N-bromosuccinimide (0.81 g, 4.60 mmol) and benzoyl peroxide (0.05 g). The reaction was heated at reflux for 18 h, cooled and filtered. The filtrate was concentrated and redissolved in anhydrous tetrahydrofuran (10 mL). Methyl thioglycolate (0.37 mL, 4.10 mmol) was added, followed by sodium hydride (80%, 0.12 g, 4.1 mmol). The reaction mixture was allowed to stir at room temperature for 3 h. Additional sodium hydride (80%, 0.14 g, 4.6 mmol) was added and the solution was heated to gentle reflux for 18 h. The reaction was cooled to 0° C. and quenched with water (20 mL). The mixture was washed with ethyl acetate (50 mL). The aqueous layer was acidified to pH 5 with acetic acid and the product extracted with ethyl acetate (3×40 mL). The organic extract was washed with brine (10 mL), dried and evaporated to provide an orange oil. Chromatography on silica gel using 6:1 hexane:ethyl acetate as eluant afforded a mixture of uncyclised compound as a yellow oil (20%) and the desired methyl 7-phenyl-8-aza-isothiochroman-4-one-3-carboxylate (23%) as a yellow solid, mp 78°–81° C. This material was heated at reflux in 3N aqueous hydrochloric acid (30 mL) for 12 h, then cooled and made basic. Extraction with ethyl acetate (4×50 mL) afforded a semi-solid mass after drying and evaporation. Chromatography on silica gel using 7:1 hexane/ethyl acetate as eluant afforded 7-phenyl-8-aza-isothiochroman-4-one as a yellow solid (68%), mp 97°–99° C.; $^1$H NMR (CDCl$_3$) δ3.58 (s, 2H), 4.14 (s, 2H), 7.48 (m, 4H), 7.78 (d, 1H), 8.04–8.07 (m, 2H), 8.40 (d, 1H); IR (KBr) 1680 cm$^1$; Mass spectrum m/z 242 (M+H); Anal. calcd. for $C_{14}H_{11}NOS$: C 69.68 H 4.54 N 5.80; Found C 69.39 H 4.58 N 5.69.

The compounds of the present invention and their preparation can be further understood by the following representative Examples, which do not constitute in any way a limitation of the present invention. All melting points are uncorrected. All reactions were conducted under a nitrogen atmosphere except where otherwise noted. All commercial chemicals were used as received. Chromatography was performed with Merck silica gel 60 (230–400 mesh). The chromatography eluents are given as ratios by volume. Organic phases from solvent-solvent extractions were generally dried over magnesium sulfate, unless otherwise noted. Solvents were generally removed by evaporation under reduced pressure on a rotary evaporator unless otherwise noted. Peak positions for $^1$H NMR spectra are reported as parts per million (8) downfield from the internal standard tetramethylsilane. Abbreviations for $^1$H NMR spectra are as follows: s=singlet, d=doublet, m=multiplet, dd=doublet of doublets, dm=doublet of multiplets. Mass spectra were obtained using chemical ionization with ammonia as the reagent gas unless otherwise noted.

EXAMPLE 1

Preparation of the compound of Formula 1 wherein $R^1$ is 6-F, $R^2$ is H, $R^3$ is 4-methylphenyl, X is $CH_2CH_2$, and $Z^1$, $Z^2$, and $Z^3$ are CH.

5-Fluoroisatin (1.40 g, 8.48 mmol) and 6-(4-methylphenyl)-1-tetralone (2.0 g, 8.47 mmol) were suspended in anhydrous ethanol. Potassium hydroxide (4.92 g, 84.8 mmol) dissolved in water (10 mL) was added and the mixture was heated at reflux overnight (approx 16 h). The mixture was cooled to room temperature and the solvent was evaporated. The residue was suspended in water (50 mL) and washed with ether (5×20 mL). The aqueous layer was acidified with hydrochloric acid (1N). The resulting precipitate was collected and triturated with a small amount of ethyl acetate to provide 1.17 g (36%) of the title compound, mp 305° C. (dec); 1H NMR (DMSO-$d_6$) δ8.55 (d, 1H), 8.28 (m, 1H), 7.85–7.68 (m, 5H), 7.60 (d, 1H), 7.38 (d, 2H), 3.18 (m, 4H), 2.40 (s, 3H); Mass spectrum 384 (M+H); High resolution mass spectrum calcd. 383.1340, found 384.1404.

EXAMPLE 2

Preparation of the compound of Formula 1 wherein $R^1$ is 6-F, $R^2$ is H, $R^3$ is 4-methylphenyl, X is $CH_2CH_2$, and $Z^1$, $Z^2$, and $Z^3$ are CH, sodium salt.

The product of Example 1 (1.17 g, 3.05 mmol) was suspended in ethanol (50 mL) and heated to reflux. Aqueous sodium hydroxide (1N; 3.05 mL, 3.05 mmol) was added dropwise during which time the material dissolved. The mixture was heated at reflux for 1 h., cooled to room temperature, filtered, and evaporated to provide the title compound as a light tan powder, mp 342° C. (dec); $^1$H NMR (DMSO-$d_6$) δ8.42 (d, 1H), 8.02 (m, 1H), 7.75–7.50 (m, 6H), 7.30 (d, 2H), 3.15–2.95 (m, 4H), 2.18 (s, 3H).

EXAMPLE 3

Preparation of the compound of Formula 1 wherein $R^1$ is 6-F, $R^2$ is H, $R^3$ is phenyl, X is $CH_2CH_2$, $Z^1$ and $Z^2$ are CH, and $Z^3$ is N, sodium salt.

2-Phenyl-7,8-dihydroquinolin-5(6H)-one (3.25 g, 14.6 mmol) and 5-fluoroisatin (2.40 g, 14.6 mmol) were suspended in ethanol (50 mL). Sodium hydroxide (3.50 g, 87.5 mmol) dissolved in water (10 mL) was added to the reaction mixture, which was then heated at reflux for 16 h. The mixture was cooled to room temperature and the solvent was evaporated. The residue was diluted with water (100 mL) and diethyl ether (100 mL) and stirred for 0.5 h. The aqueous layer was washed with diethyl ether (3×100 mL), separated and diluted with an equal volume of saturated sodium chloride solution. A precipitate formed which was collected after 1 h, washed with a small amount of water (10 mL), then triturated with acetone (50 mL), filtered and dried to provide 3.3 g (58%) of the title compound as an off-white powder, mp >350° C.; $^1$H NMR (DMSO-$d_6$) δ8.75 (d, 1H), 8.19 (d, 2H), 8.10–7.98 (m, 2H), 7.70–7.42 (m, 5H), 3.28–3.14 (m, 4H); Mass spectrum m/z 410 (M+$NH_4$), 393 (M+H); High resolution mass spectrum calc. 371.1195; found: 371.1180; Anal. calcd. for $C_{23}H_{14}FN_2O_2Na(H_2O)$: C 67.32, H 3.93, N 6.83; Found C 67.43, H 3.70, N 6.78.

EXAMPLE 4

Preparation of the compound of Formula 1 wherein $R^1$ is 6-F, $R^2$ is H, $R^3$ is phenyl, X is $CH_2CH_2$, $Z^1$ is CH, and $Z^2$ and $Z^3$ are N, sodium salt.

5-Fluoroisatin (3.30 g, 20 mmol) and 2-phenyl-7,8-dihydro-1,3-quinazolin-5(6H)-one (4.48 g, 20 mmol) were suspended in ethanol (100 mL). Sodium hydroxide (4.80 g, 120 mmol) was dissolved in water (20 mL), and added to the reaction mixture which was then heated at reflux overnight (approx 16 h). The mixture was cooled to room temperature and the solvent evaporated. The residue was diluted with water (250 mL) and filtered. The solid was washed with a small amount of water, followed by acetone (100 mL), and dried to provide 6.50 g of the title compound as an off-white powder, mp >400° C.; 1H-NMR (DMSO-$d_6$) δ9.70 (s, 1H), 8.58 (m, 2H), 8.14 (m, 1H), 7.78–7.60 (m, 5H), 3.28 dm, 4H); Anal. Calcd. for $C_{22}H_{13}FN_3O_2Na(0.5H_2O)$ C 65.67, H, 3.51, N 10.44; Found C 65.83, H 3.44, N 10.32.

EXAMPLE 22

Preparation of the compound of Formula 1 wherein $R^1$ is 6-F, $R^2$ is H, $R^3$ is phenyl, X is $CH_2S$, and $Z^1$, $Z^2$, and $Z^3$ are CH.

5-Fluoroisatin (497 mg, 3.01 mmol) and 7-phenylthiochroman-4-one (723 mg, 3.01 mmol) were suspended in ethanol (10 mL). Potassium hydroxide (1.01 g, 18 mmol) dissolved in water (1 mL) was added, and the mixture was heated at reflux overnight (approx. 16 h). The solvent was evaporated, the residue was diluted with water (10 mL) and washed with diethyl ether (2×10 mL). The aqueous layer was acidified to pH 3 with aqueous hydrochloric acid (1N), and allowed to stand for 1 h. The precipitate was collected and dried to yield 889 mg (76%) of the title compound. Recrystallization from methyl isobutyl ketone provided a light yellow powder, mp 280° C. (dec); $^1$H NMR (DMSO-$d_6$) δ8.56 (d, 1H), 8.19 (m,1H), 7.60–7.40 (m, 9H), 4.30 (s, 2H); Mass spectrum 388 (M+H); High resolution mass spectrum calcd. 387.0729, found 387.0721; Anal. calcd. for $C_{23}H_{14}FNO_2S$: C 71,30, H 3.64, N 3.62; Found C 70.84, H 3.53, N 3.51.

EXAMPLE 23

Preparation of the compound of Formula 1 wherein $R^1$ is 6-F, $R^2$ is H, $R^3$ is phenyl, X is $CH_2S$, and $Z^1$, $Z^2$, and $Z^3$ are CH, sodium salt.

The product of Example 22 (3.0 g, 7.74 mmol) was suspended in ethanol (50 mL) and heated to reflux. Aqueous sodium hydroxide (1N; 7.75 mL, 7.75 mmol) was added dropwise, during which time the material dissolved. The reaction mixture was allowed to cool to room temperature, filtered and evaporated to yield the title compound as an off-white powder, mp 230°–235° C. (dec); $^1$H NMR (DMSO-$d_6$) δ8.56 (d, 1H), 8.10 (m, 1H), 7.62–7.38 (m, 9H), 4.30 (s, 2H).

EXAMPLE 53

Preparation of the compound of Formula I wherein $R^1$ is 6-F, $R^2$ is H, $R^3$ is 4-methylphenyl, X is $CH_2O$, and $Z^1$, $Z^2$, and $Z^3$ are CH.

5-Fluoroisatin (1.00 g, 5.9 mmol) and 7-(4-methylphenyl) chroman-4-one (1.46 g, 6.1 mmol) were suspended in ethanol (30 mL). Diethylamine (445 mg, 6.1 mmol) was added and the reaction mixture stirred overnight (approx 16 h) at room temperature, during which time a precipitate formed. The precipitate was filtered, dried and dissolved in dimethoxyethane (20 mL). Water (10 mL) was added, followed by methanesulfonic acid (10 mL), and the mixture was heated at reflux overnight (approx. 16 h). The mixture was cooled to room temperature and poured into an ice-water mixture (20 mL), and allowed to stand for 1 h. The precipitate was collected and stirred with ethyl acetate (50 mL) overnight. The solid was filtered to provide 105 mg of the title compound as a light orange powder; $^1$H NMR (DMSO-$d_6$) δ8.44 (d,m 1H), 8.24 (m, 1H), 7.90–7.30 (m, 8H), 5.60 (s, 2H), 2.42 (s, 3H).

EXAMPLE 54

Preparation of the compound of Formula 1 wherein $R^1$ is 6-F, $R^2$ is H, $R^3$ is 4-methylphenyl, X is $CH_2O$, and $Z^1$, $Z^2$, and $Z^3$ are CH, sodium salt.

The product of Example 53 (100 mg, 0.25 mmol) was suspended in ethanol (10 mL) and heated to reflux. Aqueous sodium hydroxide (1N, 0.26 mL, 0.26 mmol) was added dropwise during which time the material dissolved. The mixture was heated at reflux for an additional 0.5 h, cooled to room temperature, filtered and evaporated to provide the title compound as a light tan solid, mp 305° C. (dec); $^1$H NMR (DMSO-$d_6$) δ8.44 (d, 1H) 8.10 (m, 1H), 7.95–7.35 (m, 8H), 5.44 (s, 2H), 2.42 (s,3H).

EXAMPLE 91

Preparation of the compound of Formula 1 wherein $R^1$ is 6-F, $R^2$ is H, $R^3$ is phenyl, X is $OCH_2$, and $Z^1$, $Z^2$ and $Z^3$ are CH.

A mixture of 7-phenylisochroman-4-one (0.412 g, 1.84 mmol), 5-fluoroisatin (0.303 g, 1.84 mmol), and diethylamine (0.19 mL, 1.84 mmol) was stirred in ethanol (10 mL) at room temperature under a nitrogen atmosphere for 4 h. Solvent was removed to provide a tan residue. The residue was taken up in 1,2-dimethoxyethane (10 mL) and 50% aqueous methanesulfonic acid (10 mL) was added. The mixture was heated at reflux for 18 h, cooled to room temperature and poured into water (25 mL). The aqueous solution was made basic with 1N sodium hydroxide and extracted with diethyl ether (3×25 mL). The aqueous solution was acidified with concentrated hydrochloric acid and the precipitate was collected by filtration to provide 62.5 mg (17%) of the title compound as a yellow solid, mp >250° C. (dec); $^1$H NMR (DMSO-$d_6$) δ8.42 (d, 1H), 8.16 (d of d, 1H), 7.88 (d, 1H), 7.77 (t, 3H), 7.41–7.65 (m, 5H), 5.53 (s, 2H); Mass spectrum m/z 372 (M+H); High resolution mass spectrum calc. 372.1036; found: 372.1027.

EXAMPLE 100

Preparation of the compound of Formula 1 wherein $R^1$ is 6-F, $R^2$ is H, $R^3$ is phenyl, X is $SCH_2$, and $Z^1$, $Z^2$, and $Z^3$ are CH.

Sodium hydroxide (0.49 g, 12.5 mmol) was dissolved in water (0.5 mL) and added to a solution of 5-fluoroisatin (0.34 g, 2.08 mmol) in ethanol (15 mL). The mixture was gently refluxed for 0.5 h. 7-Phenylisothiochroman-4-one was then added to the above solution in portions and the mixture was heated at reflux for 24 h. The ethanol was evaporated and the residue was diluted with water (75 mL). Unreacted starting materials were extracted with ether (2×50 mL) and discarded. The aqueous layer was treated with brine (75 mL). The precipitate that formed was filtered, washed with 2-butanone (20 mL) and dried under vacuum. The solid was dissolved in water (60 mL) and carefully acidified to pH 5 with acetic acid. The precipitate was filtered and dried under vacuum to provide the title compound as yellow crystals (52%), mp 265°–268° C. (dec); $^1$H NMR (DMSO-$d_6$) δ4.18 (s, 2H), 7.45 (d, 1H), 7.50–7.55 (ds, 2H), 7.59–7.63 (dd, 1H), 7.73–7.76 (dt, 1H), 7.78–7.84 (m, 4H), 8.21 (dd, 1H), 8.47 (d, 1H); Mass spectrum m/z 388 (M+H).

EXAMPLE 101

Preparation of the compound of Formula 1 wherein $R^1$ is 6-F, $R^2$ is H. $R^3$ is phenyl, X is $SCH_2$, and $Z^1$, $Z^2$, and $Z^3$ are CH, sodium salt.

To a solution of the compound of Example 100 (0.30 g, 0.78 mmol) in ethanol (4 mL) was added 1N aqueous sodium hydroxide (0.77 mL). The mixture was heated gently for 1 h, and the ethanol was evaporated. The residue was washed with 2-butanone (10 mL), filtered and dried under vacuum to afford the title compound (87%), mp 294°–296° C. (dec): $^1$H NMR (DMSO-$d_6$) δ4.00 (s, 2H), 7.40 (m, 1H), 7.54 (m, 3H), 7.72 (s, 1H), 7.75–7.78 (dm, 4H), 8.04 (dd, 1H), 8.46 (d, 1H); Mass spectrum m/z 388 (M+H, free acid); High resolution mass spectrum calcd. for $C_{23}H14FNO_2S$ (free acid) 388.0807.found 388.0817.

EXAMPLE 102

Preparation of the compound of Formula 1 wherein $R^1$ is 6-F, $R^2$ is H, $R^3$ is phenyl, X is $SCH_2$, $Z^1$ and $Z^2$ are CH, and $Z^3$ is N, sodium salt.

The title compound was prepared from 5-fluoroisatin and 7-phenyl-8-aza-isothiochroman-4-one in 53% yield using the procedure of Example 100, mp 210° C. dec; $^1$H NMR (DMSO-$d_6$) δ4.28 (s, 2H), 7.50–7.58 (d, 3H), 7.72–7.69 (m, 2H), 8.13–8.22 (dm, 4H), 8.71 (d, 1H); Mass spectrum m/z 389 (M+H, free acid).

The compounds of Examples 1–4, 22, 23, 53, 54, 91, and 100–102, and other compounds which have been prepared using the procedures of Examples 1–4, 22, 23, 53, 54, 91, and 100–102, and other compounds which may be prepared by such procedures are listed in Tables 1, 2, 3 and 4. In these tables, a melting point followed by the letter d indicates that decomposition occurred at the temperature or range shown.

TABLE 1

| Ex. No. | R | $R^1$ | $R^2$ | $R^3$ | X | $Z^1$ | $Z^2$ | $Z^3$ | mp °C. |
|---|---|---|---|---|---|---|---|---|---|
| 1 | H | 6-F | H | 4-$CH_3$Ph | $CH_2CH_2$ | CH | CH | CH | 305d |
| 2 | Na | 6-F | H | 4-$CH_3$Ph | $CH_2CH_2$ | CH | CH | CH | 342d |
| 3 | Na | 6-F | H | Ph | $CH_2CH_2$ | CH | CH | N | >350 |
| 4 | Na | 6-F | H | Ph | $CH_2CH_2$ | CH | N | N | >400 |
| 5 | Na | 6-F | H | 2-FPh | $CH_2CH_2$ | CH | CH | N | 257d |
| 6 | Na | 6-F | H | 2-FPh | $CH_2CH_2$ | CH | N | CH | |
| 7 | Na | 6-F | H | PhO | $CH_2CH_2$ | CH | CH | CH | 206 |
| 8 | Na | 6-F | H | 3-$CH_3$Ph | $CH_2CH_2$ | CH | CH | N | 230d |
| 9 | Na | 6-F | H | 3-$CH_3$OPh | $CH_2CH_2$ | CH | CH | N | 235d |
| 10 | H | 6-F | H | 4-$CF_3$Ph | $CH_2CH_2$ | CH | CH | CH | >350d |
| 11 | Na | 6-F | H | 4-$CH_3$OPh | $CH_2CH_2$ | CH | CH | CH | 308d |
| 12 | Na | 6-F | H | 4-$CH_3$OPh | $CH_2CH_2$ | CH | CH | CH | 350d |

TABLE 1-continued

Structure 1: Quinoline with $R^1$, $R^2$ substituents, COOR at position 4, X substituent at position 3, and at position 2 a group with $Z^1$, $Z^2$, $Z^3$, $R^3$.

| Ex. No. | R | $R^1$ | $R^2$ | $R^3$ | X | $Z^1$ | $Z^2$ | $Z^3$ | mp °C |
|---|---|---|---|---|---|---|---|---|---|
| 13 | Na | 6-F | H | 3-CH$_3$Ph | CH$_2$CH$_2$ | CH | CH | CH | 234 |
| 14 | Na | 6-F | H | 3-CH$_3$OPh | CH$_2$CH$_2$ | CH | CH | CH | 219 |
| 15 | Na | 6-F | H | 3-CH$_3$Ph | CH$_2$CH$_2$ | CH | CH | CH | 204 |
| 16 | Na | 6-F | H | 2-CH$_3$Ph | CH$_2$CH$_2$ | CH | CH | CH | 255 |
| 17 | Na | 6-F | H | 2-CH$_3$OPh | CH$_2$CH$_2$ | CH | CH | CH | 215 |
| 18 | Na | 6-F | H | 2-FPh | CH$_2$CH$_2$ | CH | CH | CH | >350 |
| 19 | Na | 6-F | H | 3-thienyl | CH$_2$CH$_2$ | CH | CH | CH | 247 |
| 20 | Na | 6-F | H | 2-thienyl | CH$_2$CH$_2$ | CH | CH | CH | 230 |
| 21 | Na | 6-F | H | 3-furyl | CH$_2$CH$_2$ | CH | CH | CH | 247 |
| 22 | H | 6-F | H | Ph | CH$_2$S | CH | CH | CH | 280d |
| 23 | Na | 6-F | H | Ph | CH$_2$S | CH | CH | CH | 230–235 |
| 24 | K | 6-F | H | Ph | CH$_2$S | CH | CH | CH | |
| 25 | H | 6-F | H | 4-FPh | CH$_2$S | CH | CH | CH | 279d |
| 26 | Na | 6-F | H | 4-CF$_3$Ph | CH$_2$S | CH | CH | CH | 237 |
| 27 | H | 6-F | H | 4-CH$_3$Ph | CH$_2$S | CH | CH | CH | 266 |
| 28 | Na | 6-F | H | 4-CH$_3$Ph | CH$_2$S | CH | CH | CH | 370–374 |
| 29 | H | 6-F | H | 4-CH$_3$OPh | CH$_2$S | CH | CH | CH | 269 |
| 30 | H | 6-CH$_3$ | H | Ph | CH$_2$S | CH | CH | CH | 308 |
| 31 | H | 6-CH$_3$ | H | 4-FPh | CH$_2$S | CH | CH | CH | 304 |
| 32 | H | 6-CH$_3$ | H | 4-CH$_3$Ph | CH$_2$S | CH | CH | CH | 306 |
| 33 | H | 6-CH$_3$ | H | 4-CH$_3$OPh | CH$_2$S | CH | CH | CH | 263 |
| 34 | H | 6-CH$_3$ | H | Ph | CH$_2$S | CH | CH | CH | 260 |
| 35 | Na | 6-CH$_3$ | H | Ph | CH$_2$S | CH | CH | CH | 254 |
| 36 | Na | 6-F | H | 3-CF$_3$Ph | CH$_2$S | CH | CH | CH | 227 |
| 37 | H | 6-F | H | 3-CH$_3$Ph | CH$_2$S | CH | CH | CH | 255–257 |
| 38 | Na | 6-F | H | 3-CH$_3$Ph | CH$_2$S | CH | CH | CH | 219 |
| 39 | H | 6-F | H | 3-CH$_3$OPh | CH$_2$S | CH | CH | CH | 225–227 |
| 40 | Na | 6-F | H | 3-CH$_3$OPh | CH$_2$S | CH | CH | CH | 239 |
| 41 | K | 6-F | H | 4-CH$_3$OPh | CH$_2$S | CH | CH | CH | |
| 42 | Na | 6-F | H | 2-FPh | CH$_2$S | CH | CH | CH | 227 |
| 43 | H | 6-F | H | 2-CH$_3$Ph | CH$_2$S | CH | CH | CH | 240 |
| 44 | Na | 6-F | H | 2-CH$_3$Ph | CH$_2$S | CH | CH | CH | |
| 45 | H | 6-F | H | 2-CH$_3$OPh | CH$_2$S | CH | CH | CH | 204 |
| 46 | Na | 6-F | H | 2-CH$_3$OPh | CH$_2$S | CH | CH | CH | |
| 47 | Na | 6-F | H | 3-thienyl | CH$_2$S | CH | CH | CH | 239 |
| 48 | Na | 6-F | H | 2-thienyl | CH$_2$S | CH | CH | CH | 325 |
| 49 | Na | 6-F | H | 3-furyl | CH$_2$S | CH | CH | CH | 331 |
| 50 | H | 6-F | H | Ph | CH$_2$O | CH | CH | CH | |
| 51 | Na | 6-F | H | Ph | CH$_2$O | CH | CH | CH | |
| 52 | Na | 6-F | H | 4-CH$_3$OPh | CH$_2$O | CH | CH | CH | 295d |
| 53 | H | 6-F | H | 4-CH$_3$Ph | CH$_2$O | CH | CH | CH | |
| 54 | Na | 6-F | H | 4-CH$_3$Ph | CH$_2$O | CH | CH | CH | 305d |
| 55 | H | 6-F | H | Ph | CH$_2$O | CH | CH | N | |
| 56 | Na | 6-F | H | 4-FPh | CH$_2$O | CH | CH | N | |
| 57 | Na | 6-F | H | 4-CH$_3$OPh | CH$_2$O | CH | CH | N | |
| 58 | Na | 6-F | H | 4-CH$_3$Ph | CH$_2$O | CH | CH | N | |
| 59 | H | 6-F | H | Ph | CH$_2$S | CH | CH | N | |
| 60 | Na | 6-F | H | Ph | CH$_2$S | CH | CH | N | |
| 61 | H | 6-F | H | 4-FPh | CH$_2$S | CH | CH | N | |
| 62 | Na | 6-F | H | 4-CF$_3$Ph | CH$_2$S | CH | CH | N | |
| 63 | H | 6-F | H | 4-CH$_3$Ph | CH$_2$S | CH | CH | N | |
| 64 | Na | 6-F | H | 4-CH$_3$Ph | CH$_2$S | CH | CH | N | |
| 65 | H | 6-F | H | 4-CH$_3$OPh | CH$_2$S | CH | CH | N | |
| 66 | H | 6-CH$_3$ | H | Ph | CH$_2$S | CH | CH | N | |
| 67 | K | 6-F | H | Ph | CH$_2$O | CH | N | N | |
| 68 | Na | 6-F | H | Ph | CH$_2$O | CH | N | N | |
| 69 | Na | 6-F | H | 4-CH$_3$OPh | CH$_2$O | CH | N | N | |
| 70 | Na | 6-F | H | 4-CH$_3$Ph | CH$_2$O | CH | N | N | |
| 71 | H | 6-F | H | Ph | CH$_2$S | CH | N | N | |
| 72 | Na | 6-F | H | Ph | CH$_2$S | CH | N | N | |
| 73 | H | 6-F | H | 4-FPh | CH$_2$S | CH | N | N | |
| 74 | K | 6-F | H | 4-CF$_3$Ph | CH$_2$S | CH | N | N | |
| 75 | H | 6-F | H | 4-CH$_3$Ph | CH$_2$S | CH | N | N | |
| 76 | Na | 6-F | H | 4-CH$_3$Ph | CH$_2$S | CH | N | N | |

TABLE 1-continued

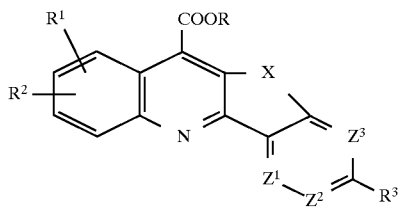

| Ex. No. | R | R¹ | R² | R³ | X | Z¹ | Z² | Z³ | mp °C. |
|---|---|---|---|---|---|---|---|---|---|
| 77 | H | 6-F | H | 4-CH₃OPh | CH₂S | CH | N | N | |
| 78 | H | 6-CH₃ | H | Ph | CH₂S | CH | N | N | |
| 79 | H | 5-Cl | H | Ph | CH₂O | CH | N | CH | |
| 80 | Na | 6-F | H | Ph | CH₂O | CH | N | CH | |
| 81 | Na | 6-F | H | 4-CH₃OPh | CH₂O | CH | N | CH | |
| 82 | Na | 6-F | H | 4-CH₃Ph | CH₂O | CH | N | CH | |
| 83 | H | 6-F | H | Ph | CH₂S | CH | N | CH | |
| 84 | Na | 6-F | H | Ph | CH₂S | CH | N | CH | |
| 85 | H | 6-F | H | 4-FPh | CH₂S | CH | N | CH | |
| 86 | Na | 6-F | H | 4-CF₃Ph | CH₂S | CH | N | CH | |
| 87 | H | 6-F | H | 4-CH₃Ph | CH₂S | CH | N | CH | |
| 88 | Na | 6-F | H | 4-CH₃Ph | CH₂S | CH | N | CH | |
| 89 | H | 6-F | H | 4-CH₃OPh | CH₂S | CH | N | CH | |
| 90 | H | 6-CH₃ | H | Ph | CH₂S | CH | N | CH | |
| 91 | H | 6-F | H | Ph | OCH₂ | CH | CH | CH | >250d |
| 92 | Na | 6-F | H | 4-CH₃Ph | OCH₂ | CH | CH | CH | |
| 93 | Na | 6-F | H | 3-CH₃Ph | OCH₂ | CH | CH | CH | |
| 94 | Na | 6-F | H | 3-CH₃OPh | OCH₂ | CH | CH | CH | |
| 95 | Na | 6-F | H | 2-CH₃Ph | OCH₂ | CH | CH | CH | |
| 96 | H | 6-CF₃ | H | Ph | OCH₂ | CH | CH | CH | |
| 97 | Na | 6-CF₃ | H | Ph | OCH₂ | CH | CH | CH | |
| 98 | Na | 6-F | H | 3-thienyl | OCH₂ | CH | CH | CH | |
| 99 | Na | 5-F | 6-F | 2-thienyl | OCH₂ | CH | CH | CH | |
| 100 | H | 6-F | H | Ph | SCH₂ | CH | CH | CH | 265–268d |
| 101 | Na | 6-F | H | Ph | SCH₂ | CH | CH | CH | 294–296d |
| 102 | Na | 6-F | H | Ph | SCH₂ | CH | CH | N | 210d |
| 103 | Na | 6-F | H | 4-CH₃Ph | SCH₂ | CH | CH | CH | 296–297d |
| 104 | Na | 6-F | H | 3-CH₃Ph | SCH₂ | CH | CH | CH | 279–801d |
| 105 | Na | 6-F | H | 3-CH₃OPh | SCH₂ | CH | CH | CH | 190–194d |
| 106 | Na | 6-F | H | 2-CH₃Ph | SCH₂ | CH | CH | CH | 285–287d |
| 107 | H | 6-CF₃ | H | Ph | SCH₂ | CH | CH | CH | 259–260 |
| 108 | Na | 6-CF₃ | H | Ph | SCH₂ | CH | CH | CH | 289–290d |
| 109 | Na | 6-F | H | 3-thienyl | SCH₂ | CH | CH | CH | 299–300d |
| 110 | Na | 6-F | H | 2-thienyl | SCH₂ | CH | CH | CH | 250–251d |
| 111 | Na | 6-F | H | 2-FPh | SCH₂ | CH | CH | N | |
| 112 | Na | 6-F | H | 3-CH₃OPh | SCH₂ | CH | CH | N | |
| 113 | Na | 5-CH₃ | 6-F | Ph | CH₂CH₂ | CH | CH | N | |
| 114 | Na | 5-CH₃ | 6-F | 2-FPh | CH₂CH₂ | CH | CH | N | |
| 115 | Na | 6-F | H | Ph | SCH₂CH₂ | CH | CH | CH | |
| 116 | Na | 6-F | H | Ph | CH₂SCH₂ | CH | CH | CH | |
| 117 | Na | 6-F | H | Ph | SCH₂ | CH | CH | N | |

TABLE 2

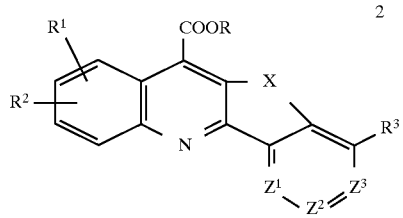

| Ex. No. | R | R¹ | R² | R³ | X | Z¹ | Z² | Z³ | mp °C. |
|---|---|---|---|---|---|---|---|---|---|
| 118 | Na | 6-F | H | Ph | CH₂CH₂ | CH | CH | CH | |
| 119 | Na | 6-F | H | PhO | CH₂CH₂ | CH | CH | CH | 191 |
| 120 | Na | 6-F | H | 2-FPh | CH₂S | CH | CH | CH | |
| 121 | Na | 6-F | H | PhO | CH₂S | CH | CH | CH | |

TABLE 2-continued

[Structure 2: Quinoline with R¹, R² substituents, COOR at 4-position, X linker at 3-position, and 2-position connected to C=C-R³ with Z¹=Z²-Z³ heterocycle]

| Ex. No. | R | R¹ | R² | R³ | X | Z¹ | Z² | Z³ | mp °C. |
|---|---|---|---|---|---|---|---|---|---|
| 122 | Na | 6-F | H | Ph | CH₂S | CH | CH | N | |
| 123 | Na | 6-F | H | PhO | CH₂S | CH | CH | N | |
| 124 | Na | 6-F | H | 3-CH₃Ph | CH₂S | CH | N | N | |
| 125 | Na | 6-F | H | 5-FPhO | CH₂S | CH | N | N | |
| 126 | Na | 6-F | H | Ph | CH₂S | CH | N | CH | |
| 127 | Na | 6-F | H | PhO | CH₂S | CH | N | CH | |
| 128 | Na | 6-F | H | 3-CH₃OPh | CH₂O | CH | CH | N | |
| 129 | Na | 6-F | H | PhO | CH₂O | CH | CH | N | |
| 130 | Na | 6-F | H | Ph | SCH₂ | CH | CH | N | |
| 131 | Na | 6-F | H | PhO | SCH₂ | CH | CH | N | |
| 132 | Na | 6-F | H | Ph | SCH₂ | CH | CH | CH | |
| 133 | Na | 6-F | H | PhO | SCH₂ | CH | CH | CH | |
| 134 | Na | 6-CF₃ | H | Ph | CH₂S | CH | CH | CH | |
| 135 | Na | 6-CF₃ | H | PhO | CH₂S | CH | CH | CH | |
| 136 | Na | 6-CF₃ | H | Ph | CH₂CH₂ | CH | CH | CH | |
| 137 | Na | 6-CF₃ | H | PhO | CH₂CH₂ | CH | CH | CH | |
| 138 | Na | 6-CF₃ | H | Ph | CH₂CH₂ | CH | CH | N | |
| 139 | Na | 6-CF₃ | H | PhO | CH₂CH₂ | CH | CH | N | |
| 140 | Na | 6-CF₃ | H | Ph | CH₂CH₂ | CH | N | N | |
| 141 | Na | 6-CF₃ | H | PhO | CH₂CH₂ | CH | N | N | |
| 142 | Na | 6-CH₃ | H | Ph | CH₂S | CH | CH | CH | |
| 143 | Na | 6-CH₃ | H | PhO | CH₂S | CH | CH | CH | |
| 144 | Na | 6-CH₃ | H | Ph | CH₂CH₂ | CH | CH | CH | |
| 145 | Na | 6-CH₃ | H | PhO | CH₂CH₂ | CH | CH | CH | |
| 146 | Na | 6-CH₃ | H | Ph | CH₂CH₂ | CH | CH | N | |
| 147 | Na | 6-CH₃ | H | PhO | CH₂CH₂ | CH | CH | N | |
| 148 | Na | 6-CH₃ | 6-F | Ph | CH₂S | CH | CH | CH | |
| 149 | Na | 6-CH₃ | 6-F | PhO | CH₂S | CH | CH | CH | |
| 150 | Na | 6-CH₃ | 6-F | Ph | CH₂CH₂ | CH | CH | CH | |
| 151 | Na | 6-CH₃ | 6-F | PhO | CH₂CH₂ | CH | CH | CH | |

TABLE 3

[Structure 3: Quinoline with R¹, R² substituents, COOR at 4-position, X linker at 3-position, and 2-position connected to C=C-Q² with Q¹-CHR³]

| Ex. No. | R | R¹ | R² | R³ | X | Q¹ | Q² | mp °C. |
|---|---|---|---|---|---|---|---|---|
| 152 | Na | 6-F | H | Ph | CH₂CH₂ | CH= | NH | |
| 153 | Na | 6-F | H | Ph | CH₂CH₂ | CH= | NCH₃ | |
| 154 | Na | 6-F | H | Ph | CH₂CH₂ | CH= | NC₂H₅ | |
| 155 | Na | 6-CF₃ | H | Ph | CH₂CH₂ | CH= | S | |
| 156 | Na | 6-CF₃ | H | Ph | CH₂CH₂ | N= | S | |
| 157 | Na | 6-CF₃ | H | Ph | CH₂CH₂ | N= | NCH₃ | |
| 158 | Na | 6-F | H | Ph | CH₂CH₂ | S | =N | |
| 159 | Na | 6-F | H | Ph | CH₂CH₂ | NCH₃ | =N | |
| 160 | Na | 6-F | H | Ph | CH₂CH₂ | S | =CH | |
| 161 | Na | 6-CF₃ | H | Ph | CH₂CH₂ | S | =N | |
| 162 | Na | 6-CF₃ | H | Ph | CH₂CH₂ | NCH₃ | =N | |
| 163 | Na | 6-CF₃ | H | Ph | CH₂CH₂ | S | =CH | |
| 164 | Na | 6-F | H | Ph | SCH₂ | CH= | NH | |
| 165 | Na | 6-F | H | Ph | SCH₂ | CH= | NCH₃ | |
| 166 | Na | 6-F | H | Ph | SCH₂ | CH= | NC₂H₅ | |
| 167 | Na | 6-CF₃ | H | Ph | SCH₂ | CH= | S | |
| 168 | Na | 6-CF₃ | H | Ph | SCH₂ | N= | S | |
| 169 | Na | 6-CF₃ | H | Ph | SCH₂ | S | =CH | |
| 170 | Na | 5-Cl | H | Ph | CH₂CH₂ | CH= | S | |
| 171 | Na | 5-Cl | H | Ph | CH₂CH₂ | N= | S | |
| 172 | Na | 6-F | H | Ph | CH₂CH₂ | NCH₃ | =CH | |
| 173 | Na | 5-CF₃ | H | Ph | CH₂CH₂ | CH= | S | |
| 174 | Na | 5-Cl | H | Ph | CH₂CH₂ | CH= | S | |
| 175 | Na | 6-F | H | Ph | SCH₂ | S | =N | |
| 176 | Na | 6-Cl | H | Ph | CH₂CH₂ | CH= | S | |

TABLE 4

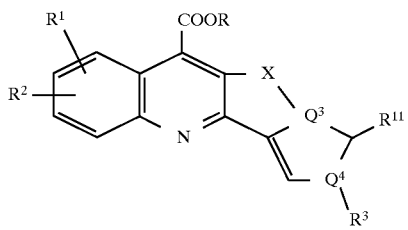

4

| Ex. No. | R | R¹ | R² | R³ | R¹¹ | X | Q³ | Q⁴ | mp °C |
|---|---|---|---|---|---|---|---|---|---|
| 177 | Na | 6-F | H | Ph | H | $CH_2CH_2$ | N | C= | |
| 178 | Na | 6-F | H | Ph | $CH_3$ | $CH_2CH_2$ | N | C= | |
| 179 | Na | 6-$CF_3$ | H | Ph | H | $CH_2CH_2$ | N | C= | |
| 180 | Na | 6-$CF_3$ | H | 2-FPh | H | $CH_2CH_2$ | N | C= | |
| 181 | Na | 6-F | H | Ph | H | $CH_2CH_2$ | C= | N | |
| 182 | Na | 6-F | H | Ph | $CH_3$ | $CH_2CH_2$ | C= | N | |
| 183 | Na | 6-$CF_3$ | H | Ph | H | $CH_2CH_2$ | C= | N | |
| 184 | Na | 6-$CF_3$ | H | Ph | $CH_3$ | $CH_2CH_2$ | C= | N | |
| 185 | Na | 6-F | H | 2-FPh | H | $CH_2CH_2$ | C= | N | |
| 186 | Na | 6-F | H | 2-FPh | $CH_3$ | $CH_2CH_2$ | C= | N | |
| 187 | Na | 6-$CF_3$ | H | 2-FPh | H | $CH_2CH_2$ | C= | N | |
| 188 | Na | 6-$CF_3$ | H | 2-FPh | $CH_3$ | $CH_2CH_2$ | C= | N | |
| 189 | Na | 6-F | H | Ph | H | $SCH_2CH_2$ | C= | N | |
| 190 | Na | 6-F | H | Ph | $CH_3$ | $SCH_2CH_2$ | C= | N | |
| 191 | Na | 6-$CF_3$ | H | Ph | H | $SCH_2CH_2$ | C= | N | |
| 192 | Na | 6-$CF_3$ | H | Ph | $CH_3$ | $SCH_2CH_2$ | C= | N | |
| 193 | Na | 6-F | H | 2-FPh | H | $SCH_2CH_2$ | C= | N | |
| 194 | Na | 6-F | H | 2-FPh | $CH_3$ | $SCH_2CH_2$ | C= | N | |
| 195 | Na | 6-$CF_3$ | H | 2-FPh | H | $SCH_2CH_2$ | C= | N | |
| 196 | Na | 6-$CF_3$ | H | 2-FPh | $CH_3$ | $SCH_2CH_2$ | C= | N | |
| 197 | Na | 6-F | H | Ph | H | $OCH_2CH_2$ | C= | N | |
| 198 | Na | 6-F | H | Ph | $CH_3$ | $OCH_2CH_2$ | C= | N | |
| 199 | Na | 6-$CF_3$ | H | Ph | H | $OCH_2CH_2$ | C= | N | |
| 200 | Na | 6-$CF_3$ | H | Ph | $CH_3$ | $OCH_2CH_2$ | C= | N | |
| 201 | Na | 6-F | H | 2-FPh | H | $OCH_2CH_2$ | C= | N | |
| 202 | Na | 6-F | H | 2-FPh | $CH_3$ | $OCH_2CH_2$ | C= | N | |
| 203 | Na | 6-$CF_3$ | H | 2-FPh | H | $OCH_2CH_2$ | C= | N | |
| 204 | Na | 6-$CF_3$ | H | 2-FPh | $CH_3$ | $OCH_2CH_2$ | C= | N | |
| 205 | Na | 6-F | H | 3-$CH_3$Ph | H | $CH_2CH_2$ | N | C= | |
| 206 | Na | 6-F | H | 3-$CH_3$OPh | H | $CH_2CH_2$ | N | C= | |
| 207 | Na | 6-$CF_3$ | H | 3-$CH_3$Ph | H | $CH_2CH_2$ | N | C= | |
| 208 | Na | 6-$CF_3$ | H | 3-$CH_3$OPh | H | $CH_2CH_2$ | N | C= | |

UTILITY

Mixed Lymphocyte Reaction

The human mixed lymphocyte reaction test described below may be used to demonstrate that the compounds of this invention have the ability to suppress or inhibit an immune cell reaction. The human mixed lymphocyte reaction is used for the determination of transplantation compatibility between the donor (graft) and the recipient (Park and Good, p. 71, in *Tissue Typing and Organ Transplantation* (Yunis et al.), 1973, Academic Press Inc., NY). The human mixed lymphocyte reaction is an in vitro immune response. Inhibition of the human mixed lymphocyte reaction immune response is a standard assay used in the field of immunology, which is considered to be indicative of in vivo immunosuppressive activity. In particular, activity in the mixed lymphocyte reaction indicates that the compounds of the present invention should be effective in preventing organ transplantation rejection and graft vs. host disease. The human mixed lymphocyte is also used as a model system for immune reactions involving T-cell-mediated immune responses. Such T-cell-mediated immune responses have been linked to the disease pathology associated with autoimmune diseases, chronic inflammatory diseases, graft versus host disease and organ transplantation rejection. Thus, in view of the results presented in the application, the compounds of Formulas 1–4 of the present invention are expected to be efficacious in treating these diseases.

Blood was obtained by venipuncture from two non-related human donors. Peripheral blood mononuclear cells (PBMC) were isolated from these samples by using the Leuco Prep procedure (Becton-Dickinson). PBMC were washed twice in phosphate buffered saline (without calcium and magnesium) and the separate cell isolations were adjusted to the appropriate concentrations in media (RPMI 1640) supplemented with 10% human AB serum and 50 $\mu$l/mL gentamicin. Cells from donor A ($2\times10^5$) were incubated with cells from donor B ($2\times10^5$) with or without compound in 96 well round bottom microtiter plates at 37° C., 5% $CO_2$ for 6 days. Eighteen hours prior to harvesting cells from the plates, all wells were pulsed with 1 $\mu$Ci of triturated-thymidine. Cells from the plates were washed on day 6 and triturated-thymidine incorporation was determined using a scintillation counter.

MLR test results for representative compounds of the present invention are shown in Table 5. In this table, ++ indicates an $IC_{50}$ value less than $5\times10^{-8}$M, and + indicates an $IC_{50}$ value in the range $5\times10^{-8}$M to $1\times10^{-5}$M.

TABLE 5

| Compound | MLR Activity |
| --- | --- |
| cyclosporin A | ++ |
| methotrexate | ++ |
| Example 1 | ++ |
| Example 2 | ++ |
| Example 3 | + |
| Example 5 | + |
| Example 8 | + |
| Example 9 | + |
| Example 10 | + |
| Example 11 | + |
| Example 12 | + |
| Example 13 | + |
| Example 14 | ++ |
| Example 16 | ++ |
| Example 17 | ++ |
| Example 18 | ++ |
| Example 19 | + |
| Example 20 | ++ |
| Example 21 | + |
| Example 22 | + |
| Example 25 | + |
| Example 26 | + |
| Example 27 | ++ |
| Example 28 | ++ |
| Example 29 | + |
| Example 30 | + |
| Example 31 | + |
| Example 32 | + |
| Example 34 | + |
| Example 35 | ++ |
| Example 37 | ++ |
| Example 38 | ++ |
| Example 39 | ++ |
| Example 40 | ++ |
| Example 42 | ++ |
| Example 43 | ++ |
| Example 45 | ++ |
| Example 47 | ++ |
| Example 48 | ++ |
| Example 50 | + |
| Example 51 | + |
| Example 51 | ++ |
| Example 52 | + |
| Example 54 | ++ |
| Example 101 | + |
| Example 103 | + |
| Example 105 | + |
| Example 107 | + |
| Example 108 | + |

The testing results in the human mixed lymphocyte proliferation reaction test show that the compounds of the present invention suppress or inhibit an in vitro immune response (i.e., have potent immunosuppressive activity) and should be efficacious in the treatment and/or prevention of organ transplantation rejection, graft versus host disease, psoriasis, rheumatoid arthritis, autoimmune diseases, and chronic inflammatory diseases, which all involve T-lymphocyte immune responses. Also, the antiproliferative activity of the compounds of the present invention indicates the utility of these compounds for the inhibition of tumor growth.

Contact Sensitivity Response to DNFB in Mice

Contact sensitivity to DNFB has been extensively studied and characterized in the mouse to determine the regulatory mechanisms involved in cell mediated immune responses (Claman et al., *Immunol. Rev.* 50:105, 1980; Young and Young, "Cutaneous Models of Inflammation for the Evaluation of Topical and Systemic Pharmacological Agents" in *Pharmacological Methods in the Control of Inflammation* (Chang and Lewis, Eds.), Alan R. Liss, Inc., New York, pp 215–231, 1989). This is an antigen-specific T-cell mediated inflammatory response that represents delayed-type hypersensitivity reactions seen in both humans and other mammals. The contact sensitivity animal model is used routinely in many laboratories for pharmacological screening of anti-inflammatory agents and agents for the treatment of autoimmune diseases.

Balb/c female mice ($\approx$20 g, Charles River) were sensitized on the shaved abdomen with 25 $\mu$L of 0.5% 2,4-dinitrofluorobenzene (DNFB) (Eastman Kodak Co.) in a vehicle of 4:1 acetone:olive oil on days 0 and 1. Mice were ear challenged with 20 $\mu$L of 0.2% DNFB in a vehicle of 4:1 acetone:olive oil on day 5. An identical segment of the ear was measured immediately before challenge and 24 hours later with an engineer's micrometer. Ear swelling was expressed as the difference in ear thickness before and after challenge in units of 10–4 inches±SEM. Percent suppression was calculated as:

$$\% \text{ Suppression} = 1 - \frac{\text{compound treated} - \text{negative control}}{\text{positive control} - \text{negative control}} \times 100$$

Compounds (prepared in 0.25% Methocel®) were administered orally. Control animals received only vehicle (0.25% Methocel®). Negative controls were not sensitized on days 0 and 1 but were ear challenged on day 5. Ten mice are typically used per group.

Contact sensitivity results for representative compounds of the present invention are shown in Table 6. In this table, + designates greater than 30% suppression of control ear swelling.

TABLE 6

| Compound | Contact Sensitivity Activity |
| --- | --- |
| cyclosporin A | + |
| methotrexate | + |
| Example 14 | + |
| Example 22 | + |
| Example 23 | + |
| Example 34 | + |
| Example 35 | + |
| Example 51 | + |

Results of the biological tests shown above demonstrate that the carbocylic and heterocyclic fused-ring quinolinecarboxylic acid compounds of Formulas 1–4 of the present invention have the effect of suppressing or inhibiting the contact sensitivity response to 2,4-dinitrofluorobenzene (DNFB) in mice.

Contact sensitivity to DNFB is a form of delayed-type hypersensitivity which has been extensively studied to gain an understanding of the regulation of immunologic processes (Claman et al., supra). This reaction is mediated by T lymphocytes that become sensitized to antigen by proliferating and developing into mature effector cells (Claman et al., supra). This cell-mediated immune response (T-cell mediated immunity) is central to many disease states such as organ transplantation rejection and graft versus host disease (Benacerraf and Unanue (1979), *Textbook of Immunology*, Williams & Wilkins Co.; Eisen (1980), *Immunology, An Introduction to Molecular and Cellular Principles of the Immune Responses*, Harper & Row, Inc.; Loveland and McKenzie (1982), *Immunology*, 46:313–320; Gallin et al. (1988), *Inflammation, Basic Principles and Clinical Correlates*, Raven Press).

The contact sensitivity model used for this study is a model system for delayed-type hypersensitivity reactions which have been linked to the disease pathology associated with organ transplantation rejection, graft versus host disease, multiple sclerosis, myasthenia gravis, systemic lupus erythematosus, rheumatoid arthritis, and other chronic inflammatory diseases and autoimmune diseases for which the T-cell is pivotal to mounting an immune or autoimmune response.

The contact sensitivity model is an extensively used model system for delayed-type hypersensitivity reactions involving cell-mediated immune responses (T-cell-mediated responses), which have been linked to organ transplantation rejection and graft versus host disease, as well as the disease pathology associated with psoriasis, rheumatoid arthritis, autoimmune diseases, and chronic inflammatory disease states. Since all of these diseases are known to involve T-lymphocyte components the claimed immunosuppressive compounds of Formulas 1–4 are expected to be efficacious in treating these diseases.

The present results show that the compounds useful in this invention have both immunomodulating and anti-inflammatory effectiveness.

Adjuvant-Induced Arthritis

Rat adjuvant-induced arthritis represents a systemic inflammatory disease with bone and cartilage changes similar to that observed in rheumatoid arthritis, but in an accelerated time span (Pearson, *Arth. Rheum.* 7:80, 1964). Activity of test compounds in the adjuvant-induced arthritis model is indicative of anti-inflammatory activity for the treatment of chronic inflammatory diseases such as rheumatoid arthritis, psoriasis, and inflammatory bowel disease.

Male Lewis rats (Charles River) weighing 160–210 grams are injected subcutaneously with 0.1 mL of Freund's complete adjuvant containing 5 mg of M. butyricum/mL of paraffin oil (Difco Laboratories) into the plantar region of the right hind paw. Paraffin oil is injected for non-arthritic controls. Ten rats are typically used per group. Compounds are prepared in 0.25% Methocel® (Dow Chemical Co.) with one drop of Tween® 80 per 10 mL of Methocel®. Animals are dosed every day beginning on the day of paw injection until day 18. The weight of each animal is recorded every other day beginning on the day of the paw injections. On day 18 the animals are weighed, and the non-injected hind paw volume is measured using a Ugo Basile Volume Differential Plethysmometer.

TPA-Induced Hyperproliferation

The TPA-induced hyperproliferation test described below may be used to establish that the compounds of the present invention have the ability to inhibit skin hyperplasia induced by the repeated application of tetradecanoyl phorbol acetate (TPA) to mouse ears (Marks et al., *Cancer Res.*, 36:2636, 1976). TPA is known to induce changes in murine skin which mimics many of the inflammatory and epithelial changes which occur in human skin diseases such as psoriasis.

CF-1 male mice (Charles River; weight: 20–25 g) are treated orally with test compound prepared in 0.25% Methocel® (Dow Chemical Co.) one hour prior to the application of 1 µg of TPA (in acetone) to the right ear with acetone only to the left ear. This treatment is repeated once a day for a total of 4 consecutive days. On day 5, the animals are injected intraperitoneally with 2 mg/kg of vinblastine sulfate to arrest dividing cells in metaphase. Four hours later, the animals are sacrificed and the ears removed for histological processing. The histological slides were then examined in a light microscope and the metaphase figures per millimeter basement membrane counted. Ten mice are typically used per group.

The test results may be used to show that the compounds described herein effectively suppress the mitotic activity associated with mouse skin hyperplasia induced by TPA, indicative of efficacy in treating human skin and muco-epithelial diseases such as psoriasis (in all its forms), lichen, chronic eczema, icthyosis, pityriasis and chronic uticaria.

Anti-cancer Activity

Representative compounds of the present invention may be tested in a variety of pre-clinical animal tumor models of anti-cancer activity, described below, which are indicative of clinical utility. The anti-tumor activity may also be tested in the in vitro cell growth inhibitory assay described below.

In Vitro Growth Inhibitory Activity

The reagents for tissue culture are purchased from GIBCO (Grand Island, N.Y.). 5-(Dimethylthiazol-2-yl)-2,5-diphenyl tetrazolium bromide (MTT) was purchased from Sigma Chemical Company (St. Louis, Mo.). All agents are prepared as 2 mg/mL stock solutions in DMSO. MTT is prepared as a 1 mg/mL stock solution in Dulbecco's phosphate buffered saline (PBS). All stocks are stored frozen in the dark at $-20°$ C.

Clone A human colon cancer cells were isolated from the heterogeneous DLD-1 colon tumor line and maintained as previously described (Dexter et al. *Cancer Research* 1979, 39, 1020; Dexter et al. *Am. J. Med.* 1981, 71, 949.). Murine leukemia L1210 cells are maintained in RPMI-L medium as described (Chen et al. *Cancer Research* 1986, 46, 5014.). All cell lines were incubated at 37° C. in a humidified atmosphere of 5% $CO_2$-95% air.

Exponentially growing L1210 cells ($1 \times 10^3$), or Clone A cells ($8 \times 10^2$) in 0.1 mL medium are seeded in a 96-well microtiter plate on day 0. On day one, 0.1 mL aliquots of medium containing graded concentrations of test compounds are added to the cell plates. After incubation at 37° C. in a humidified incubator for 72 hr, the plates containing L1210 cells are centrifuged briefly and 100 µL of the growth medium was removed. Cell cultures are incubated with 50 µL of MTT for 4 h at 37° C. The resulting purple formazan precipitate is solubilized with 200 µL of 0.04N HCl in isopropyl alcohol. Absorbance is read in a Titertek Multiskan MCC scanning well spectrophotometer (Flow Laboratories) at a test wavelength of 570 nm and a reference wavelength of 630 nm. $IC_{50}$ values are determined by a computer program that fits the data to the following equation:

$$Y=((A_m-A_o)/(1+(X/IC_{50})^n))+A_o$$

where $A_m$=absorbance of the control cells; $A_o$=absorbance of the cells in the presence of highest compound concentration; Y=observed absorbance; X=compound concentration; $IC_{50}$=dose of compound that inhibits the number of population doublings of cells to one half that of the number of population doublings of the control cells; and n equals the slope of the straight portion of the curve.

Animal Tumor Models

In the animal tumor models described below the anti-tumor activity of the compounds of the present invention may be assessed using one or more of the parameters described below.

In the tumor growth inhibition assay the efficacy of test compounds is determined by the extent of tumor growth inhibition in treated versus vehicle-treated control mice. Tumor weights (mg) are estimated from caliper measurements, using the formula for a prolate ellipsoid (mg of tumor weight (length×width$^2$)/2). Net tumor weights are calculated for each of the treated groups and the vehicle-treated control group by subtracting the initial tumor weight from the final tumor weight when the experiment is terminated. Results are expressed using the formula:

$$\% \text{ Tumor Growth Inhibition} = \left[1 - \frac{\text{mean tumor weight of treated}}{\text{mean tumor weight of control}}\right] \times 100$$

In survival studies the anti-tumor activity is expressed using the formula:

$$\% T/C \text{ (survival)} = \frac{[\text{MEAN SURVIVAL TIME OF TREATED}]}{[\text{MEAN SURVIVAL TIME OF CONTROLS}]} \times 100$$

In tumor growth delay assays the T/C value was calculated as the median time (days) required for the treated group to reach a predetermined size (750 mg) divided by the median time required for the control group tumors to reach the same predetermined size:

$$\% T/C \text{ (tumor growth delay)} = \frac{\left[\begin{array}{c}\text{MEAN TIME FOR TREATED}\\\text{GROUP TO REACH TUMOR SIZE}\end{array}\right]}{\left[\begin{array}{c}\text{MEAN TIME FOR UNTREATED}\\\text{GROUP TO REACH TUMOR SIZE}\end{array}\right]} \times 100$$

In some cases tumor growth delay is expressed in "days" calculated by subtracting the median time in days for control group tumors to reach a predetermined weight from the median time for treated group tumors to grow to the same predetermined weight.

In experiments using mouse leukemia models, the activity of test compounds may also be expressed as the percent increase in host life span (% ILS) using the formula:

$$\% ILS = \frac{\left[\begin{array}{c}\text{mean survival time treated group} -\\\text{mean survival time control group}\end{array}\right]}{[\text{mean survival time control group}]} \times 100$$

For subcutaneously growing tumors, the tumor cell kill is calculated as follows:

$$\text{Log}_{10} \text{ kill (total)} = \frac{[T - C \text{ (days)}]}{(3.32)(TD)}$$

where T-C is the tumor growth delay and TD is the tumor doubling time in days.

In the tumor models described below there are usually 5–10 mice per group of animals.

B16Melanoma Model: The B16 tumor line arose spontaneously on the skin at the base of the ear in a $C_{57}BL$ mouse (NIH Publication No. 84-2635, February, 1984, In Vivo Cancer Models). The tumor line is maintained subcutaneously (s.c.) by serial passage in female C57BL mice. For testing, on day 0, female B6C3F1 mice weighing 18–22 gm. are inoculated intraperitoneally with 0.25 mL of the 1:5 tumor brei. Mice are randomized into groups. A 0.25% Methocel®/2% Tween® 80 vehicle is used for control and compound formulation. Test compounds and vehicle control are administered intraperitoneally once daily for nine consecutive days beginning on day 1.

P388 Leukemia Model: The P388 tumor line originated in a lymphocytic leukemia in a female DBA/2 mouse after painting the skin with 3-methyl-cholanthrene (NIH Publication No. 84-2635, February, 1984, In Vivo Cancer Models). The tumor line is maintained by serial passage in female DBA/2 mice. For testing, on day 0, female CDF1 mice weighing 18–22 gm are inoculated i.p. with $1\times10^6$ viable P388 cells harvested from the ascites of passage DBA/2 mice. The mice are randomized into groups. Vehicle control and test compounds are administered i.p. or i.v. once daily for five or nine consecutive days beginning on day 1 (route and days predetermined). A 0.25% Methocel®/2% Tween® 80 vehicle was used for control and compound formulation.

L1210 Leukemia Model: The L1210 tumor line was originally chemically induced in 1948 in the spleen and lymph nodes of a DBA mouse by painting the skin with methylcholanthrene in ethyl ether (NIH Publication No. 84-2635, February 1984: In Vivo Cancer Models). The tumor line is maintained by serial passage in female DBA/2 mice. For testing, on day 0, female CDF1 mice weighing 18–22 gm are inoculated i.p. with $1\times10^5$ L1210 cells (0.1 mL/mouse) harvested from the ascites of DBA/2 mice. The mice are randomized into groups. Vehicle control and test compounds are administered i.p. or i.v. once daily for five or nine consecutive days beginning on day 1 (route and days predetermined). A 0.25% Methocel®/2% Tween® 80 vehicle is used for control and compound formulation.

Pancreatic Ductile Adenocarcinoma (Panc02 and Panc03): The pancreatic ductal adenocarcinoma tumor line originated from a tumor induced by implant of thread carrying 3-methyl-cholanthrene into the pancreas tissue of a mouse (Corbett et al., *Cancer Research* (1984) 44: 717–726). Tumor fragments are implanted s.c. bilateral by trocar and the test compounds are administered i.v., p.o., or s.c. beginning 1–3 days after implantation, on a once or twice daily schedule.

Mouse Mammary Adenocarcinoma 16/C (Mam16/C): The mouse mammary adenocinoma 16/C was originally isolated and maintained in a serial passage by transplantation of metastatic lung foci (Corbett et al., *Cancer Treat. Rep.* (1978) 62: 1471–1488). Tumor fragments are implanted s.c. bilaterally by trocar and 1–3 days later treatment with test compounds was begun. Compounds are administered once or twice daily. Tumors are measured with calipers once or twice weekly. Mice are sacrificed when tumors in the control group exceeded an average weight of 1,500 mg.

Mouse Mammary Adenocarcinoma 17 (Mam17): This tumor line is maintained in the Developmental Therapeutics Program frozen repository, maintained by the Biological Testing Branch, Frederick, Md. (Mucci-LoRusso et al., *Investigational New Drugs* (1990) 8(3): 253–261). Chemotherapy studies in C3H female mice bearing Mam17 tumors are conducted in the same manner as described above for the Mam16/C tumor.

Subcutaneously-implanted Colon 38 Carcinoma (Colon38) and Colon 51 Carcinoma (Colon51): These tumor lines originated from a tumor chemically induced in the colon of C57BL/6 mouse, induced by repeated s.c. injections of 1,2-dimethylhydrazine (Corbett et al., *Cancer Research* (1975) 35: 2434–2439). Tumor fragments are implanted bilaterally s.c. by trocar and 1–3 days after implantation treatment with test compound is started. Compounds are administered once or twice daily. Tumors are measured with calipers once or twice weekly until tumors in the control group exceed an average weight of 1,500 mg.

In Vivo Human Tumor Xenograft Models (MX-1, LX-1, CX-1, and DLD-2)

The MX-1 human mammary carcinoma, LX-1 human lung carcinoma, and CX-1 and DLD-2 human colon carcinoma were originally obtained from a surgically removed primary breast tumor, lung tumor, and colon carcinomas, respectively. The human tumor lines are maintained by serial passage in athymic nude mice. The MX-1 human mammary carcinoma is an established tumor used by the NCI. The MX-1 and DLD-2 tumor models have been well characterized.

The mice used may be outbred Swiss mice or BALB/c mice bearing the nude (nu/nu) gene. On day 0, 30–60 tumor fragments are implanted subcutaneously bilaterally by trocar in female mice (20–25 g). Tumor fragments are prepared from fresh tumors grown subcutaneously in passage mice. Palpable tumors weighing approximately 50 mg appear in the mice within 7–10 days after inoculation. The mice grouped and the test compounds and vehicle control are administered intravenously (iv) once daily on days 3, 5, 7, and 12–16.

Tumor measurements and body weights are recorded once or twice a week. Mice are sacrificed when tumors reach an average weight of 1,500 mg (about day 20).

The efficacy of the test compounds is measured as the % Tumor Growth Inhibition. The criteria of the National Cancer Institute for activity in the in vivo cancer models were used (NIH Publication No. 84-2635, February 1984: In Vivo Cancer Models). Actual tumor regressions (IR=incomplete regression; FR=full regression) indicate excellent to outstanding activity. Tumor growth inhibition of 290% is considered good to excellent and inhibition of 58–89% is considered moderate to good. Compounds demonstrating <58% growth inhibition are considered inactive.

Dosage and Formulation

The compounds of the present invention can be administered to treat or prevent organ transplantation rejection, graft versus host disease, psoriasis, autoimmune diseases and chronic inflammatory diseases, by any means that produces contact of the active agent with the agent's site of action in the body of a mammal. The compounds of the present invention can also be administered to treat skin and muco-epithelial diseases such as psoriasis (in all its forms), lichen, chronic eczema, icthyosis, pityriasis and chronic uticaria. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

Suitable pharmaceutical carriers and methods of preparing pharmaceutical dosage forms are described in *Remington's Pharmaceutical Sciences,* Mack Publishing Company, a standard reference text in this field.

As is appreciated by a medical practitioner skilled in the art, the dosage administered will vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. By way of general guidance, a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Pharmaceutical compositions (dosage forms) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active ingredient usually contain suitable carriers, diluents, preservatives, or other excipients, as described in *Remington's Pharmaceutical Sciences,* Mack Publishing Company, a standard reference text in the field.

Gelatin capsules contain the active ingredient and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

The topical ointments, creams, gels, and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or anti-oxidizing agents. The compounds of the present invention can be administered in a topical dosage form in combination with steroid drugs, particularly topical steroids such as Synalar (fluocinolone acetonide), Lidex (fluocinolone), Westcort (hydrocortisone valerate), Valisone (betamethasone valeate), and Diprasone (betamethasone dipropionate).

Powders and sprays can contain the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Examples of useful pharmaceutical compositions (dosage forms) for administration of the compounds of this invention are provided below.

Capsules: Capsules may be prepared by filling standard two-piece hard gelatin capsules each with 50 mg of powdered active ingredient, 175 mg of lactose, 24 mg of talc, and 6 mg of magnesium stearate.

Soft Gelatin Capsules: A mixture of active ingredient in soybean oil is prepared and injected by means of a positive displacement pump into gelatin to form soft gelatin capsules containing 50 mg of the active ingredient. The capsules are washed in petroleum ether and dried.

Tablets: Tablets may be prepared by conventional procedures so that the dosage unit is 50 mg of active ingredient, 6 mg of magnesium stearate, 70 mg of microcrystalline cellulose, 11 mg of cornstarch, and 225 mg of lactose. Appropriate coatings may be applied to increase palatability or delay absorption.

Suspension: An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable: A parenteral composition suitable for administration by injection is prepared by stirring 1.5% by weight of active ingredient in 10% by volume propylene glycol and water. The solution is sterilized by commonly used techniques.

Nasal Spray: An aqueous solution is prepared such that each 1 mL contains 10 mg of active ingredient, 1.8 mg methylparabel, 0.2 mg propylparaben and 10 mg methylcellulose. The solution is dispensed into 1 mL vials.

Lung Inhaler: A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

Ointment: The active ingredient is added to a mixture of 48% by weight white petrolatum, 10% liquid petrolatum, 8% glycerol monostearate, 3% isopropyl myristate, and 20% lanolin at 70° C. After thorough mixing, a warm solution of methyl- and propyl-parabens in water containing sodium acetone bisulfite is added such that the final concentrations of each paraben is 0.15%, of water is 8%, and of sodium acetone bisulfite is 0.5%. The mixture is stirred until it has reached room temperature.

Topical Formulations: An ointment for topical administration may also prepared at 70° C. by adding the active ingredient to a mixture of 48% by weight white petrolatum, 10% liquid petrolatum, 8% glycerol monostearate, 3% isopropyl myristate and 20% lanolin. After thorough mixing, a warm solution of methyl and propyl parabens in water containing sodium acetone bisulfite is added such that the final concentrations of each paraben is 0.15%, of water is 8% and of sodium acetone bisulfite is 0–5%. The mixture is stirred until it has reached room temperature.

A cream for topical administration is prepared at 75° C. by adding the active ingredient to a mixture of 1% sodium lauryl sulfate, 12% propylene glycol, 25% stearyl alcohol, 25% white petrolatum and 37% water. The mixture is stirred until it congeals.

A gel for topical administration is prepared at 70° C. by adding the active ingredient to a mixture of 0.75% Carbopol 940 (polycarbopol), 46.25% water, 3% emulsifier hydroxylated lanolin, 50% ethanol and, optionally, 1–2% diisopropanolamine. The mixture is stirred until it cools to room temperature.

Pharmaceutical kits which comprise a therapeutically effective amount of a pharmaceutical composition comprising a compound of Formulas 1–4 in one or more sterile containers, are also within the ambit of the present invention. Sterilization of the container may be carried out using conventional sterilization methodology well known to those skilled in the art. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the therapeutic agent to be administered, guidelines for administration, and/or guidelines for mixing the components, may also be included in the kit.

The compounds of Formulas 1–4 (component (i)) can be administered in combination with a second immunosuppressive agent (component (ii)) as a combination treatment by any conventional means available for the use in conjunction with pharmaceuticals, either as individual separate dosage units administered simultaneously or concurrently, or in a physical combination of each component therapeutic agent in a single or combined dosage unit.

Such second immunosuppressive agent (component (ii)) may be selected from the group consisting of, but not limited to: cyclosporin A, azathioprine, corticosteroids such as prednisone, OKT3, FK506, mycophenolic acid or the 2-(N-morpholino)ethyl ester thereof, 15-deoxyspergualin, rapamycin, mizoribine, misoprostol and anti-interleukin-2 (IL-2) receptor antibodies. The combination treatment can be administered to treat immuno-modulatory disorders and inflammatory diseases and particularly to prevent or treat organ transplantation rejection, graft versus host disease, psoriasis, rheumatoid arthritis, autoimmune diseases, and chronic inflammatory diseases, and related disorders, by any means that produces contact of the active ingredient(s) with the agent's site of action in the body of a mammal.

As discussed above, the dosage administered in the combination treatment will vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired.

By way of general guidance, usually a daily oral dosage of each active ingredient can be about 0.001 to 1000 mg/kg of body weight. Ordinarily a dose of 0.1 to 100 mg/kg per day in divided doses one to six times a day or in sustained release form may be effective to obtain the desired results.

The active ingredients in the combination therapy can be administered in various dosage forms, optionally with a pharmaceutical carrier, and different dosage routes as discussed above for the single agent therapy.

The component (i) and (ii) of the invention may be formulated together, in a single dosage unit (that is, combined together in one capsule, tablet, powder, or liquid, etc.) as a combination product. When component (i) and (ii) are not formulated together in a single dosage unit, the compound of Formulas 1–4 (component (i)) may be administered at the same time as the second immunosuppressive agent (component (ii)) or in any order; for example component (i) of this invention may be administered first, followed by administration of component (ii), or they may be administered in the reverse order. When not administered at the same time, preferably the administration of component (i) and (ii) of this invention occurs less than about one hour apart. Preferably, the route of administration of component (i) and (ii) of the invention is oral. The terms oral agent, oral inhibitor, oral compound, or the like, as used herein, denote compounds which may be orally administered. Although it is preferable that component (i) and component (ii) of the invention are both administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (i) and (ii) in this invention will be readily ascertainable by a medical practitioner skilled in the art, based upon the present disclosure. By way of general guidance, typically a daily dosage may be about 100 milligrams to about 1 gram of each component. By way of general guidance, when the compounds of component (i) and component (ii) are administered in combination, the dosage amount of each component may be reduced by about 70–80% relative to the usual dosage of the component when it is administered alone as a single agent.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Representative compounds of the invention useful for the treatment of transplantation rejection, graft versus host disease, psoriasis, autoimmune diseases and inflammatory diseases are listed in the Tables 1–4.

What is claimed is:

1. A compound of Formula 1 or 2:

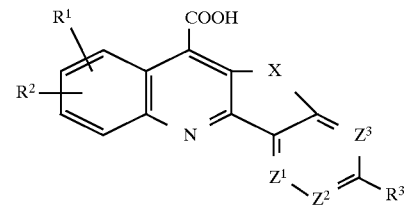

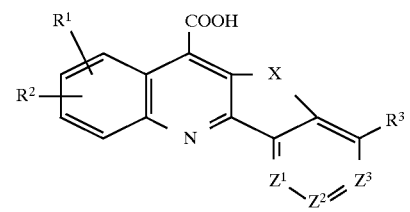

or a pharmaceutically acceptable salt form thereof, wherein:
$R^1$ and $R^2$ are independently H, F, Cl, Br, $CF_3$, or allyl of 1–4 carbons;
$R^3$ is selected from, phenyl, phenoxy, phenylthio, phenylsulfinyl, phenyl-$N(R^4)$—, furyl, thienyl, pyridyl, thiazolyl, or oxazolyl, wherein said phenyl, phenoxy, phenylthio, phenylsulfinyl, phenyl-$N(R^4)$—, furyl, thienyl, pyridyl, thiazolyl, or oxazolyl is substituted with 0–2 groups independently selected from: F, Cl, Br, $CF_3$, alkyl of 1–4 carbons, alkoxy of 14 carbons, alkylthio of 14 carbons or alkylsulfinyl of 14 carbons;

$R^4$ is H, alkyl of 1–4 carbons or acyl of 14 carbons;

X is —Y—, —$CH_2Y$—, —$YCH_2$—, —$CR^6$=N—, or —N=$C(R^6)$— (the first atom of X as listed being attached to the quinoline ring); wherein each methylene group in X may be optionally substituted with one or two groups independently selected from alkyl of 1–4 carbons;

Y is —$CH_2$— (said —$CH_2$— being optionally and independently substituted with one or two alkyl groups of 1–4 carbons), —O—, —S—, or —$N(R^7)$—;

$R^5$ and $R^6$ are independently H or alkyl of 1–4 carbons;

$R^7$ is H, alkyl of 1–4 carbons, or acyl of 1–4 carbons, wherein, in compounds of Formula 1 and Formula 2:

one of $Z^1$, $Z^2$ and $Z^3$ is N, and the remaining $Z^1$, $Z^2$ and $Z^3$ are $CR^8$;

$R^8$ is independently selected from H, F, Cl, Br, $CF_3$, or alkyl of 1–4 carbons;

subject to the following provisos:
1) X is not $NR^7$;
2) in compounds of Formula 1, when X is —$CH_2CH_2$— and each of $Z^1$, $Z^2$ and $Z^3$ is CH, then $R^3$ is not unsubstituted phenyl.

2. A compound of claim 1, wherein:

$R^1$ is 6-F or 6-$CF_3$;

$R^2$ is H;

$R^3$ is phenyl, thienyl or furyl; said phenyl, thienyl or furyl being substituted with 0–2 groups independently selected from: F, Cl, Br, $CF_3$, alkyl of 1–4 carbons, alkoxy of 1–4 carbons, alkylthio of 1–4 carbons or alkylsulfinyl of 1–4 carbons, X is —$CH_2CH_2$—, —$CH_2S$—, —$SCH_2$—, —$CH_2O$—, or —$OCH_2$—;

wherein, in compounds of Formula 1 or Formula 2, $Z^1$ is CH.

3. A compound of claim 2, or a pharmaceutically acceptable salt form thereof, wherein:

$R^3$ is phenyl, 2-fluorophenyl, 3-methoxyphenyl, 3-methylphenyl, 3-trifluoromethylphenyl, or thienyl.

4. A compound of claim 1, or a pharmaceutically acceptable salt form thereof, selected from the following:

(g) the compound of Formula 1 where $R^1$ is 6-F; $R^2$ is H; $R^3$ is phenyl; $Z^1$ and $Z^2$ are CH; $Z^3$ is N; and X is $CH_2CH_2$, or a sodium salt;

(i) the compound of Formula 1 where $R^1$ is 6-F; $R^2$ is H; $R^3$ is phenyl; $Z^1$ and $Z^2$ are CH; $Z^3$ is N; and X is $SCH_2$, or a sodium salt.

5. A pharmaceutical composition comprising a compound of claim 1 and a pharmaceutically acceptable carrier.

6. A pharmaceutical composition comprising a compound of claim 2 and a pharmaceutically acceptable carrier.

7. A pharmaceutical composition comprising a compound of claim 3 and a pharmaceutically acceptable carrier.

8. A pharmaceutical composition comprising a compound of claim 4 and a pharmaceutically acceptable carrier.

9. A method of treating organ transplantation rejection, graft versus host disease, psoriasis, rheumatoid arthritis, autoimmune diseases, or chronic inflammatory diseases in a mammal comprising administering to the mammal in need of such treatment a therapeutically effective amount of a compound of claim 1.

10. A method of treating organ transplantation rejection, graft versus host disease, psoriasis, rheumatoid arthritis, autoimmune diseases, or chronic inflammatory diseases in a mammal comprising administering to the mammal in need of such treatment a therapeutically effective amount of a compound of claim 2.

11. A method of treating organ transplantation rejection, graft versus host disease, psoriasis, rheumatoid arthritis, autoimmune diseases, or chronic inflammatory diseases in a mammal comprising administering to the mammal in need of such treatment a therapeutically effective amount of a compound of claim 3.

12. A method of treating organ transplantation rejection, graft versus host disease, psoriasis, rheumatoid arthritis, autoimmune diseases, or chronic inflammatory diseases in a mammal comprising administering to a mammal in need of such treatment a therapeutically effective amount of a compound of claim 4.

13. A method of treating organ transplantation rejection or graft versus host disease in a mammal comprising administering in combination to a mammal in need of such treatment a therapeutically effective amount of: (i) a compound of claim 1; and (ii) at least one additional immunosuppressive agent.

14. The method of claim 13 wherein the additional immunosuppressive agent (ii) is selected from the group consisting of cyclosporin A, azathioprine, a corticosteriod, OKT3 (monoclonal antibody), FK506 (tacrolimus), mycophenolic acid or the 2-(N-morpholino)ethyl ester thereof, mycophenolate mofetil, 15-dioxyspergualin, rapamycin, mizoribine, leflunomide, misoprostol, methotrexate, cyclophosphamide, anti-lymphocyte/thymocyte serums or an anti-interleukin-2 receptor antibody.

15. A method of treating rheumatoid arthritis, systemic lupus erythematosus, multiple sclerosis, myasthenia gravis, organ transplantation rejection, graft versus host disease, or a chronic inflammatory disease in a mammal comprising administering to a mammal in need of such treatment, a therapeutically effective amount of a nonsteroidal antiinflammatory drug in combination with a compound of claim 1.

16. A method of treating a skin or muco-epithelial disease in a mammal comprising administering to a mammal in need of such treatment, a therapeutically effective amount of a compound of claim 1.

17. A method of claim 16 wherein the compound of claim 1 is administered in combination with a steroid drug.

18. A topical pharmaceutical composition comprising a carrier suitable for topical formulation and a therapeutically effective amount of a compound of claim 1.

19. A method of treating a solid tumor, lymphoma, or a leukemia in a mammal comprising administering to a mammal in need of such treatment, a therapeutically effective amount of a compound of claim 1.

* * * * *